United States Patent
Zingaretti et al.

(10) Patent No.: US 9,486,290 B2
(45) Date of Patent: *Nov. 8, 2016

(54) METHODS AND SYSTEMS FOR MODIFYING A PARAMETER OF AN AUTOMATED PROCEDURE

(75) Inventors: Gabriele Zingaretti, Capitola, CA (US); Mohan Bodduluri, Palo Alto, CA (US); Miguel G. Canales, Los Altos, CA (US); Brian E. Tippett, Coto de Caza, CA (US); Hui Zhang, San Jose, CA (US)

(73) Assignee: Restoration Robotics, Inc., San Jose, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 13/978,344

(22) PCT Filed: Jan. 6, 2012

(86) PCT No.: PCT/US2012/020549
§ 371 (c)(1),
(2), (4) Date: Jul. 3, 2013

(87) PCT Pub. No.: WO2012/094637
PCT Pub. Date: Jul. 12, 2012

(65) Prior Publication Data
US 2013/0287286 A1    Oct. 31, 2013

Related U.S. Application Data

(63) Continuation-in-part of application No. 13/161,396, filed on Jun. 15, 2011, now Pat. No. 8,951,266.

(60) Provisional application No. 61/430,864, filed on Jan. 7, 2011, provisional application No. 61/430,864, filed on Jan. 7, 2011.

(51) Int. Cl.
*G06K 9/00* (2006.01)
*A61B 19/00* (2006.01)
(Continued)

(52) U.S. Cl.
CPC ........... *A61B 19/5244* (2013.01); *A45D 26/00* (2013.01); *A61B 17/3468* (2013.01);
(Continued)

(58) Field of Classification Search
None
See application file for complete search history.

(56) References Cited

U.S. PATENT DOCUMENTS 3,867,942 A    2/1975 Bellantoni et al.
4,431,007 A    2/1984 Amazeen et al.
(Continued)

FOREIGN PATENT DOCUMENTS

CN    101505659 A    8/2009
CN    101506825 A    8/2009
(Continued)

OTHER PUBLICATIONS

European Search Report and European Search Opinion, in connection with commonly assigned European Patent Application No. 12732235.2, EPO Forms 1507S, 1503, P0459 and 1703, dated Sep. 6, 2013. (5 pages).
(Continued)

*Primary Examiner* — Chan Park
*Assistant Examiner* — Iman K Kholdebarin
(74) *Attorney, Agent, or Firm* — Sharon Upham; Lena I. Vinitskaya

(57) ABSTRACT

A variety of systems and methods are described which enable quantitative information to be extracted regarding automated procedures, including those performed at a high speed that may require a user input, without having to interrupt the procedure. In addition, these systems and methods serve to provide information on one or more parameters of the automated procedure, whereby they may be modified, if required, to improve the automated procedure or the results from such a procedure. The systems and methods provided are especially useful in automated hair transplantation procedures.

43 Claims, 5 Drawing Sheets

(51) Int. Cl.
*G06T 7/00* (2006.01)
*A45D 26/00* (2006.01)
*A61B 17/34* (2006.01)
*A61B 17/00* (2006.01)

(52) U.S. Cl.
CPC .............. *A61B34/20* (2016.02); *A61B 34/30* (2016.02); *G06T 7/0004* (2013.01); *A61B 90/37* (2016.02); *A61B 2017/00203* (2013.01); *A61B 2017/00207* (2013.01); *A61B 2017/00752* (2013.01); *A61B 2017/00969* (2013.01); *A61B 2034/743* (2016.02)

(56) References Cited

U.S. PATENT DOCUMENTS

| | | | |
|---|---|---|---|
| 5,857,031 A * | 1/1999 | Zelt, III | B23D 35/007 382/108 |
| 6,585,746 B2 | 7/2003 | Gildenberg | |
| 6,676,654 B1 | 1/2004 | Balle-Petersen et al. | |
| 7,107,090 B2 | 9/2006 | Salisbury et al. | |
| 7,477,782 B2 * | 1/2009 | Qureshi | G06K 9/00127 382/171 |
| 7,526,747 B2 * | 4/2009 | Nishiyama | G01N 23/203 716/51 |
| 7,611,452 B2 | 11/2009 | Allison et al. | |
| 7,676,061 B2 * | 3/2010 | Harrison | B23K 26/032 382/100 |
| 8,048,090 B2 * | 11/2011 | Qureshi | A61F 2/10 606/133 |
| 8,389,892 B2 * | 3/2013 | Hinrichs | B23K 26/03 219/121.7 |
| 8,512,356 B2 * | 8/2013 | Oostman, Jr. | A61B 17/32053 606/133 |
| 8,690,895 B2 * | 4/2014 | Oostman, Jr. | A61B 17/32053 606/133 |
| 8,951,266 B2 * | 2/2015 | Zingaretti | G06T 7/0004 606/133 |
| 8,951,267 B2 * | 2/2015 | Oostman, Jr. | A61B 17/00 606/133 |
| 2001/0034530 A1 * | 10/2001 | Malackowski | A61B 34/20 606/130 |
| 2002/0193849 A1 * | 12/2002 | Fenn | A61N 5/02 607/89 |
| 2004/0152972 A1 | 8/2004 | Hunter | |
| 2004/0193203 A1 | 9/2004 | Pak et al. | |
| 2005/0096515 A1 | 5/2005 | Geng | |
| 2007/0106306 A1 * | 5/2007 | Bodduluri | A61B 17/32053 606/133 |
| 2007/0106633 A1 | 5/2007 | Reiner | |
| 2007/0127795 A1 | 6/2007 | Lau et al. | |
| 2007/0167801 A1 | 7/2007 | Webler et al. | |
| 2007/0171365 A1 * | 7/2007 | Tuan | A61B 3/107 351/205 |
| 2008/0013678 A1 * | 1/2008 | Magerl | A61B 90/50 378/20 |
| 2008/0064953 A1 | 3/2008 | Falco et al. | |
| 2008/0144023 A1 * | 6/2008 | Shibata | G01N 21/21 356/237.2 |
| 2009/0005765 A1 * | 1/2009 | Oostman, Jr. | A61B 17/32053 606/9 |
| 2009/0080733 A1 * | 3/2009 | Qureshi | G06K 9/00127 382/128 |
| 2009/0125050 A1 | 5/2009 | Dixon | |
| 2009/0306498 A1 | 12/2009 | Bodduluri et al. | |
| 2010/0025336 A1 | 2/2010 | Carter et al. | |
| 2010/0081875 A1 * | 4/2010 | Fowler | A61B 1/00149 600/114 |
| 2010/0082039 A1 | 4/2010 | Mohr et al. | |
| 2010/0169815 A1 | 7/2010 | Zhao et al. | |
| 2010/0198402 A1 * | 8/2010 | Greer | A61B 19/201 700/247 |
| 2010/0234871 A1 * | 9/2010 | Qureshi | A61F 2/10 606/187 |
| 2010/0249777 A1 | 9/2010 | Sherman et al. | |
| 2010/0256479 A1 | 10/2010 | Park et al. | |
| 2010/0256504 A1 | 10/2010 | Moreau-Gaudry et al. | |
| 2010/0294747 A1 * | 11/2010 | Hinrichs | B23K 26/03 219/121.71 |
| 2011/0060321 A1 | 3/2011 | Chandler et al. | |
| 2011/0105898 A1 | 5/2011 | Guthart et al. | |
| 2011/0116703 A1 | 5/2011 | Fu et al. | |
| 2011/0160589 A1 | 6/2011 | Fu et al. | |
| 2011/0276046 A1 * | 11/2011 | Heimbecher | A61B 18/1492 606/35 |
| 2012/0179189 A1 * | 7/2012 | Zingaretti | G06T 7/0004 606/187 |
| 2012/0209257 A1 * | 8/2012 | van der Weide | A61B 18/1815 606/23 |
| 2012/0296343 A1 * | 11/2012 | Bodduluri | A61F 2/10 606/133 |
| 2013/0024213 A1 * | 1/2013 | Poon | A61B 5/0002 705/3 |
| 2013/0150992 A1 * | 6/2013 | Hinrichs | B23K 26/03 700/97 |
| 2013/0287286 A1 * | 10/2013 | Zingaretti | G06T 7/0004 382/141 |
| 2014/0276958 A1 * | 9/2014 | Zhang | A61B 19/5225 606/133 |
| 2014/0355834 A1 * | 12/2014 | Qureshi | G06T 7/2033 382/103 |
| 2015/0112364 A1 * | 4/2015 | Zingaretti | G06T 7/0004 606/130 |

FOREIGN PATENT DOCUMENTS

| | | |
|---|---|---|
| CN | 101523426 A | 9/2009 |
| CN | 101801279 A | 8/2010 |
| CN | 101926678 | 12/2010 |
| JP | 2002-541973 | 11/2000 |
| JP | 2010-279714 | 12/2010 |
| WO | 00/64379 | 11/2000 |
| WO | WO 2005/009215 | 2/2005 |
| WO | 2007/041267 | 4/2007 |
| WO | WO 2008/024954 | 2/2008 |
| WO | WO 2008/024955 | 2/2008 |
| WO | WO 2008/043091 | 4/2008 |
| WO | WO 2009/045255 | 4/2009 |
| WO | WO 2010/104718 | 9/2010 |

OTHER PUBLICATIONS

PCT International Search Report and Written Opinion for PCT/US2012/020549 from the International Search Authory, Applicant Restoration Robotics, Forms PCT/ISA/210, 220, and 237, mailed Jul. 27, 2012 (15 pages).

Office Action Mailed Aug. 25, 2014, in connection with commonly assigned Canadian Patent Application No. 2,821,343, Restoration Robotics, Inc. (4 pages).

Office Action mailed Jul. 7, 2014, in connection with commonly assigned Australian Patent Application No. 2012204163 (3 pages).

English Translation of Office Action mailed Jul. 1, 2014, in connection with commonly assigned Japanese Patent Application No. 2013-547733 (2 pages).

Office Action mailed Mar. 19, 2014, in connection with commonly assigned U.S. Appl. No. 13/161,396, (9 pages).

English Translation of Office Action mailed Dec. 10, 2013 in connection with commonly assigned, Japanese Patent Application No. 2013-547733, Restoration Robotics, Inc. (5 pages).

English Translation of Office Action mailed Dec. 17, 2013, in connection with commonly assigned Korean Patent Application No. 10-2013-7017818, Restoration Robotics Inc., (2 pages).

Office Action Mailed Mar. 31, 2015, in connection with commonly assigned Canadian Patent Application No. 2,821,343, Restoration Robotics, Inc. (6 pages).

English Translation of Chinese Office Action mailed Dec. 1, 2014, in connection with commonly assigned Chinese Patent Application No. 201280004260.5.

English Translation of Notice of Rejection in connection with commonly assigned Japanese Patent Application No. 2014-224529, mailed Oct. 27, 2015, (2 pages).

(56) References Cited

OTHER PUBLICATIONS

Communication Pursuant to Article 94(3) EPC, in connection with commonly assigned European Patent Application No. 12 732 235.2, mailed Aug. 21, 2015 (4 pages).

English Translation of Office Action mailed Mar. 1, 2016, in connection with commonly assigned Japanese Patent Application No. 2013-547733, (4 pages).

Communication Pursuant to Article 94(3) EPC, in connection with commonly assigned European Patent Application No. 12 732 235.2, mailed Mar. 22, 2016, 4 pages.

\* cited by examiner

METHODS AND SYSTEMS FOR MODIFYING A PARAMETER OF AN AUTOMATED PROCEDURE

RELATED APPLICATION DATA

This Application is a U.S. National Stage filing under 35 U.S.C. §371 of International Application No. PCT/US2012/020549, filed Jan. 6, 2012, which is a continuation-in-part of U.S. patent application Ser. No. 13/161,396, filed Jun. 15, 2011, which claims benefit of U.S. Provisional Application Ser. No. 61/430,864 filed Jan. 7, 2011. Priority to the aforementioned applications is hereby expressly claimed in accordance with 35 U.S.C. §§119, 120, 365 and 371 and any other applicable statutes.

FIELD OF THE INVENTION

The present application relates generally to automated procedures and more particularly to methods and systems for displaying and modifying a parameter of an automated procedure, such as a hair transplantation procedure, using imaging and processing techniques.

BACKGROUND OF THE INVENTION

There are various medical and cosmetic procedures that may be performed now using various degrees of automation often at a high speed, in some instances using hand-held automated tools, in other instances utilizing automated systems that may include robotic arms, for example. In such procedures, in order to ensure that the automated procedures provide the results desired, user input may be required from time to time. These procedures include, for example, automated hair removal using lasers of varying intensities and wavelengths, or tattoo removal using lasers, including lasers of varying intensities and wavelengths, as disclosed for example in the commonly assigned U.S. Patent Publication No. 2008/0247637.

Another such procedure is a hair transplantation procedure. Hair transplantation procedures typically involve harvesting hair grafts from a donor area, for example, the patient's scalp, and implanting them in a recipient or bald area. Automated hair transplantation systems utilizing a robot, including a robotic arm and a hair follicle tool associated with the robotic arm are disclosed, for example, in U.S. Pat. No. 6,585,746 which describes an automated hair transplantation system utilizing a robot, including a robotic arm and a hair follicle introducer associated with the robotic arm. This system can be used to harvest follicular units from a donor area or implant follicular units into a recipient area with computer assistance.

SUMMARY OF THE INVENTION

In accordance with one general aspect, the present application discloses systems and methods that could be used to analyze and modify, if needed, one or more parameters of the automated procedure. In some embodiments, a method for determining a need to modify a parameter of an at least partially automated procedure is provided. The method comprises providing a real-time image of a surface having an at least partially automated procedure performed thereon and also providing at least one snapshot of the surface, the snapshot identifying or allowing to identify a parameter of the automated procedure. The method further comprises determining the need to modify the same or a different parameter of the automated procedure to improve results of the procedure. The method may further comprise modifying the identified parameter or a different parameter. For example, the same or a different parameter may be modified if a value of the parameter in the snapshot suggests that a change is required or desirable, for example, the value of the parameter falls outside an acceptable limit or a range, or is otherwise not advantageous. In some embodiments the value of the parameter may be modified or adjusted by a user, in other embodiments, the modification may be performed automatically. The method may comprise displaying the real-time image and/or the least one snapshot of the surface. The method may comprise providing a modification interface that allows a user to modify one or more parameters of the automated procedure. The above method may be implemented, for example, in a hair harvesting or hair implantation procedure, or in an automated tattoo removal procedure, various ablation procedures, cosmetic injection procedures, ophthalmic procedures, treating various dermatological conditions, or any other procedure that could benefit from the inventions described herein.

According to certain embodiments, a method for modifying a parameter of an at least partially automated procedure, for example hair transplantation procedure, is provided. The method comprising (in reference to hair transplantation example) providing a real-time image of a body surface having an at least partially automated hair transplantation procedure performed thereon; providing at least one snapshot of the body surface, the at least one snapshot allowing to identify whether a criteria associated with the at least partially automated procedure is met; and modifying at least one parameter associated with the at least partially automated procedure if the criteria is not met. For example, with reference to hair harvesting, the at least one parameter may be modified to improve hair follicle dissection.

According to another aspect, the present application provides a method for determining a need to modify a parameter of an automated procedure. The method comprising providing a snapshot of a body surface, the snapshot displaying, for example, an indication of a maximum depth or angle of penetration of a tool (e.g., hair transplantation tool) with respect to the body or tissue surface. The method further comprises allowing for comparison of the displayed indication of depth or angle of penetration (or insertion) against an intended value of depth or angle of penetration/insertion and based on the comparison for determination of whether an adjustment of the depth or the angle of insertion is required.

According to yet another aspect, a method is provided for automatically or semi-automatically modifying (or determining the need to modify) a tool approach angle or a tool penetration depth in an at least partially automated procedure, for example, a procedure on a patient's body. The method comprises providing or processing information to enable modification of the tool approach angle or the tool penetration depth, if certain conditions are met.

According to a further aspect, the present application provides an apparatus or a system comprising a processor configured or designed to perform one or more of the inventive methods. The system may also comprise a memory adapted to store, at least temporarily, at least one image. In certain embodiments, the system further comprises an interface adapted to receive one or more images, for example, of a body surface where procedure is performed, for example, from which follicular units are being harvested and/or where hair grafts are to be or being implanted. In certain embodiments, the system may further comprise an image acquisition device, while in other embodiments the system may be a part of a robotic system, such as robotic system for hair transplantation.

According to a still further aspect, there is provided a method for orienting a tool for transplanting follicular units, comprising: choosing a minimum approach angle of a tool based at least in part on an average or mean emergence angle of a plurality of follicular units in an area; determining an emergence angle of a follicular unit of interest; comparing the emergence angle of the follicular unit of interest with the minimum approach angle of the tool; and determining orientation of the tool based on a result of the comparison of the emergence angle of the follicular unit of interest with the minimum approach angle of the tool. The method may further comprise orienting the tool based on the result of the comparison of the emergence angle of the follicular unit of interest with the minimum approach angle of the tool.

In still another aspect, the present application provides machine-readable media on which are provided program instructions for performing one or more of inventive processes or methods described herein.

Other and further objects, features and advantages of the invention will become apparent from the following detailed description when read in view of the accompanying figures.

BRIEF DESCRIPTION OF THE DRAWINGS

It should be noted that the drawings are not to scale and are intended only as an aid in conjunction with the explanations in the following detailed description. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Features and advantages of the present invention will become appreciated as the same become better understood with reference to the specification, claims, and appended drawings wherein:

DETAILED DESCRIPTION OF THE PREFERRED EMBODIMENTS

Figure 1:
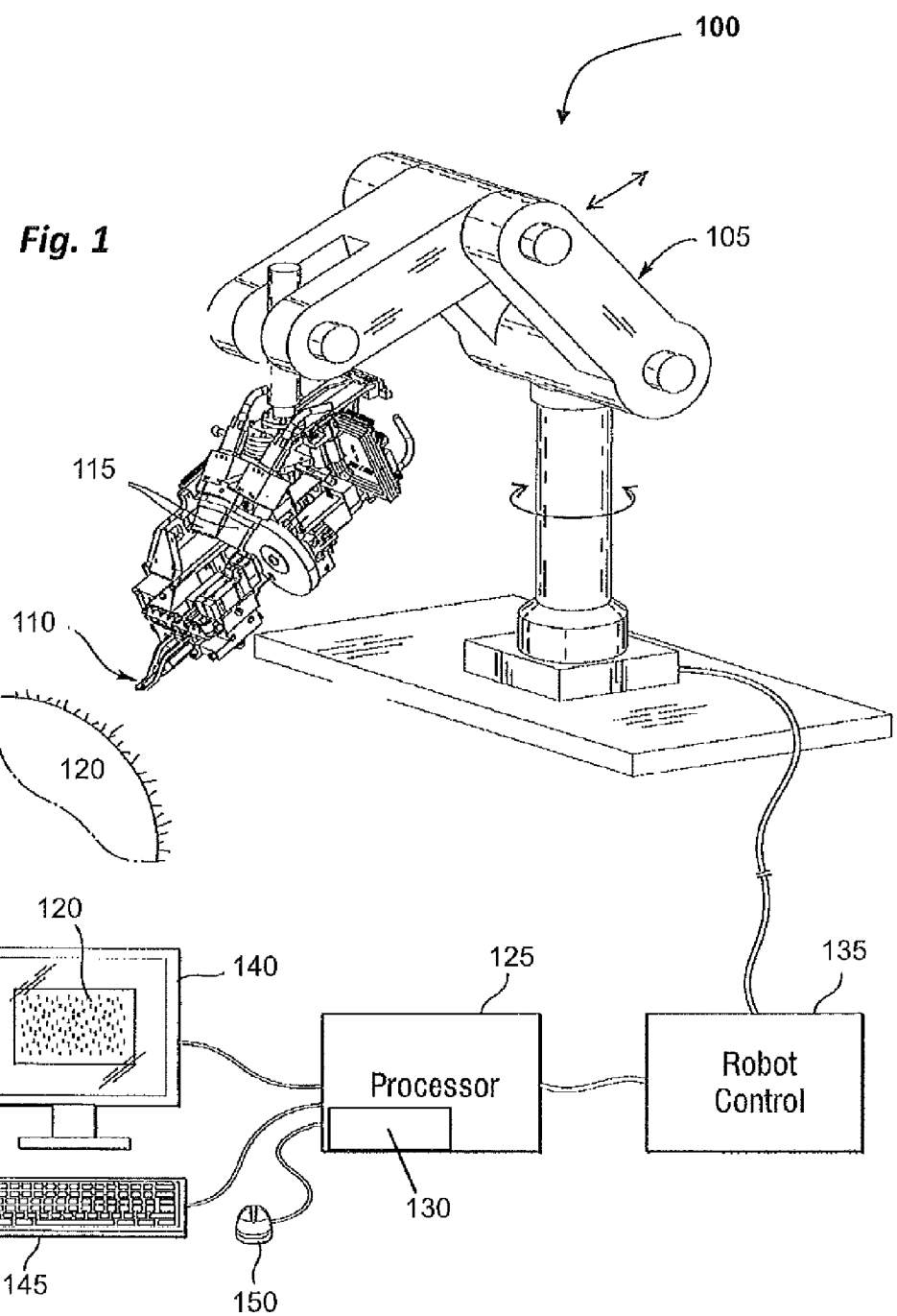
FIG. 1 is a schematic representation of an example of a robotic system that could be implemented in various embodiments of the inventions described herein.

In the following Detailed Description, reference is made to the accompanying drawings that show by way of illustration some examples of embodiments in which the invention may be practiced. It is to be understood that other embodiments may be utilized and structural or logical changes may be made without departing from the scope of the present invention. In this regard, directional terminology, such as "outer", "inner", "higher", "lower", "first", "second" etc., are used with reference to the orientation of the Figure(s) being described. Because components or embodiments of the present invention can be positioned or operated in a number of different orientations, the directional terminology is used for purposes of illustration and is in no way limiting. The following description, therefore, is not to be taken in a limiting sense, and the scope of the present invention is defined by the appended claims.

The term "tool", "harvesting tool" or "implantation tool", as used herein in reference to hair transplantation, refers to any number of tools or end effectors that are capable of creating implantation sites, dissecting, harvesting or implanting follicular units ("FUs") from a body surface. Such tools may have many different forms and configurations. In many embodiments, the tool comprises a hollow tubular shaft and thus may be labeled, for example, a cannula, a needle, or a punch. The distal ends of such tools (for example, punches, coring devices, cutting and/or trimming devices, needles), are typically sharpened, to various degrees, to assist in creating implantation sites or harvesting or implanting the follicular unit. Other tools applicable for alternative procedures that could benefit from the inventions of the present application may comprise, for example, lasers, or tattoo removal tools, surgical scalpels, forceps, hemostats, surgical instruments, retractors, electrosurgical tools, radiofrequency ablation tools, suturing devices, eye speculum, or drills.

Embodiments of the methods of the present invention may be implemented using computer software, firmware or hardware. Various programming languages and operating systems may be used to implement the inventions described herein.

It should be understood that various inventive concepts described herein may be applied to a variety of procedures and applications. For convenience of description, the following description will be discussed by example in reference to hair transplantation procedures. Hair transplantation procedures that are carried out using automated (including robotic) systems or computer-controlled systems have been described, for example, in the commonly assigned Publication No. US 2007/0106306 which is incorporated herein by reference. Robotic hair transplantation systems generally require accurate positioning of a tool under robotic control. When implementing a semi-automated or a fully automated procedure it is likely that modification to certain parameters may be required. According to one aspect disclosed herein, the present application provides methodology that enables modifications to be made to the value of parameters, for example parameters associated with the hair transplantation procedure, such that the modifications may be made easily, and without necessarily interrupting the procedure itself.

One of the benefits of an automated hair transplantation system is to substantially reduce the time of the procedure while performing hundreds of repetitive and tedious steps associated with hair harvesting and/or hair implantation procedures. One of the consequences of using an automated hair transplantation system, however, is that the speed at which the automated hair transplantation process occurs may be too fast for the doctor who directs the automated system to easily observe its operation, discern certain parameters, and make any necessary adjustments of the parameters of harvesting or implantation process. Since skin tension, or hair follicles' density, thickness, and many other parameters may vary from patient to patient, and even within different areas of the scalp of the same patient, the surgeon's input is required, for example, to adjust the depth or the angle of the insertion of the tool, to ensure the transplantation is successful (e.g., the follicular units are harvested without transecting or otherwise damaging them). The automated systems may be operating so quickly that unless the doctor is willing to temporarily halt the procedure, he may not be able to tell if any adjustment to the process is required, before it is too late, and the procedure has been completed or is well under way. With an example of a hair transplantation procedure, in addition to the system requirements and considerations, consideration of various aspects of the patient involved also have to be dealt with. For example, all body surfaces are not as elastic as others, some may be formed of tissue that is easily penetrated by a harvesting tool, whereas other tissue may be more difficult to penetrate, even if a similar force is applied over a similar time period to the surface to puncture the skin. Therefore the need to adjust a parameter of the hair transplant procedure from one patient to another, or from one portion of a donor area to another is to be expected, especially when performed by the automated tools or robotic systems. Should any adjustment be necessary, typically, a certain amount of time is often lost when the automated process is interrupted to check to see if adjustment is necessary, or to actually make the necessary adjustment. If the initial adjustment does not solve the issue, further interruption will also be required until the problem is solved. The utilization of automated systems and methods for hair transplantation, therefore create other issues in their endeavor to improve the speed and efficiency of the automated procedure.

According to the various embodiments described herein, a variety of systems and methods have been developed which enable quantitative information to be extracted regarding the procedure without having to interrupt the procedure. In addition, these systems and methods serve to provide information on one or more parameters of the procedure, whereby they may be modified, if required, for example with reference to hair harvesting, to improve the hair harvesting procedure or the results from such a procedure. In one configuration, for example, the system allows the user to visually inspect a magnified image of the harvested hair(s) and based on the inspection, the user may approve or modify one or more parameters to enhance the system's performance, or the results from such a procedure. In another configuration, for example, the system may automatically carry out such "visual" inspection of the "image" of the harvested hair(s) and automatically modify one or more parameters to enhance the system's performance, or the results from such a procedure. The visual inspection may be based on the capture of quantitative parameters of previous harvesting or implantation attempts, such parameters including but not limited to the angle of the tool, the depth of penetration of the tool, the force applied to the tool during penetration, whether the dissected follicular unit was retained in the harvesting tool, whether the follicular unit was transected during the dissection, and/or the rotational speed of the tool. For example, image processing may be utilized to identify whether a follicular unit was retained in the harvesting tool. The system may be configured to take a snapshot at an instance when the tool is retracted from the body surface, and the image processor may be configured or programmed to check an absence of a follicular unit (if there is cavity in the body surface from which the follicular unit was removed), or if the follicular unit is still present to some degree. Based on the finding, the processor may then automatically determine (without input from the user) if any modification to one or more of the associated parameters is required and automatically instruct the required modification accordingly. In this manner, the system is able to automatically carry out a "visual" inspection of the "image" of the harvested hair(s) and automatically modify one or more parameters to enhance the system's performance. In certain embodiments or configurations the systems and methods described herein may use a combination of the user inspection and user input with the automated inspection and automated modification of the parameters of the relevant procedures. The identification of a value associated with various parameters, and the modification thereof, enables the user (or the system, or both combined), for example, to modify the angle at which the tool is inserted into the body surface, the depth to which it is inserted, the force applied on insertion, the selection of tool size, and/or the rotational speed of the tool, to thereby minimize damage during the procedures, for example any damage to the follicular unit being removed, and/or improve the quality of the removed specimen, preferably preserving its integrity. These systems and methods may also serve to reduce the transection rate of follicular units during the dissection process. These systems and methods can be incorporated into the use of or as part of an automated or semi-automated system, and/or of part of a computer or robotically controlled system. The modifications identified above can be carried out in a timely manner to avoid continuous operation under the undesirable parameters, and they could be performed without having to interrupt or substantially delay the automated transplantation procedure.

Although the various examples and embodiments described herein will use follicular units or hairs for purposes of describing the various aspect of the invention, it should be apparent that the general understanding of the various concepts discussed can be applied more broadly to other appropriate applications. It should be understood that although the methods described herein are especially suited for use with a robotic system for hair harvesting and/or implanting, they can be applied to other applications. These additional applications may include, for example, an automated tattoo placement or removal, or an automated hair removal, various ablation procedures, cosmetic injection procedures, ophthalmic procedures, treating various dermatological conditions, or any other procedure that could benefit from the inventions described herein. It should be noted that the examples given herein are for the purposes of illustration and example only, the description as set forth is not intended to be exhaustive or limiting.

FIG. 1 is a schematic perspective view of an example of a robotic system 100 for harvesting and/or implanting follicular units into a body surface, such as the scalp. The system 100 includes a robotic arm 105 to which is coupled a harvesting or implanting tool 110. Various motors and other movement devices may be incorporated to enable fine movements of an operating tip of the tool 110 in multiple directions. The robotic system 100 further includes at least one (and preferably two for stereo vision) image acquisition device 115 which may be mounted in a fixed position, or coupled (directly or indirectly) to a robotic arm 105 or other controllable motion device. The operating tip of the tool 110 is shown positioned over a body surface 120, in this case a part of the patient scalp having hair follicles thereon.

The processor 125 of FIG. 1 comprises an image processor 130 for processing images obtained from the image acquisition device 115. The image processor 130 may be a separate device or it may be incorporated as a part of the processor 125. The processor 125 may also instruct the various movement devices of the robotic arm 105, including the tool 110, and act, for example, through a controller 135 as schematically shown in FIG. 1. The controller 135 may be operatively coupled to the robotic arm and configured to control the motion of the robotic arm, including the motion based on the images or data acquired by the image acquisition device. Alternatively, controller 135 may be incorporated as a part of the processor 125, so that all processing and controls of all movements of all the tools, the robotic arm and any other moveable parts of the assembly, including those based on the images or data acquired by the image acquisition device, are concentrated in one place. The system 100 may further comprise a monitor 140, keyboard 145, and mouse 150. A magnified image of the body surface 120 can be seen on the imaging display or monitor 140. In addition, the system 100 may comprise other tools, devices and components useful in harvesting, and/or implantation of the hair follicles, or in hair treatment planning. The system further comprises an interface (not shown) adapted to receive an image data, various parts of the system allow an operator to monitor conditions and provide instructions, as needed. The processor 125 may interact with the imaging device 115 via the interface. The interface may include hardware ports, cables, leads, and other data transmission means, or it may comprise a computer program.

Some non-limiting examples of an image acquisition device 115 shown in FIG. 1 include one or more cameras, such as any commercially available cameras. The image acquisition or imaging device may be held, for example, by a robotic arm, or by any other mechanism or means. Of course, various image acquisition devices or a combination of several devices could be used with any of the embodiments of the systems and methods described herein. The image acquisition device 115 may comprise a device that takes still images, it can also comprise a device capable of real time imaging (e.g., webcam capable of continuously streaming real time information), and/or it could also have a video recording capability (such as a camcorder). While stereo or multi-view imaging devices are very useful in the present invention, it is not necessary to employ such geometries or configurations, and the present invention is not so limited. Likewise, although it is preferred that the image acquisition device be a digital device, it is not necessary. For example, the image acquisition device could be an analog TV camera that acquires an initial image which is then processed into a digital image (for example, via an analog-to-digital device like a commercial-off-the-shelf frame grabber) for further use in the method of the present invention. The image acquisition device may be coupled to a processing system 125, shown incorporated in the image processor 130 in FIG. 1, to control the imaging operation and process image data.

Typically, the processor 125 operates as a data processing device, for example, it may be incorporated into a computer. The processor 125 may include a central processing unit or parallel processor, and input/output interface, a memory with a program, wherein all the components may be connected by a bus. Further, the computer may include an input device, a display, and may also include one or more secondary storage devices. The bus may be internal to the computer and may include an adapter for receiving a keyboard or input device or may include external connections.

The processor 125 may execute a program that may be configured to include predetermined operations. The processor may access the memory in which may be stored at least one sequence of code instructions comprising the program for performing predetermined operations. The memory and the program may be located within the computer or may be located external thereto. By way of example, and not limitation, a suitable image processor 130 may be a digital processing system which includes one or more processors or other type of device. For example, a processor and/or an image processor may be a controller or any type of personal computer ("PC"). Alternatively, the processor may comprise an Application Specific Integrated Circuit (ASIC) or Field Programmable Gate Array (FPGA). It will be understood by those of ordinary skill in the art that the processor and/or the image processor for use with the present invention is programmed and configured to perform various known image processing techniques, for example, segmentation, edge detection, object recognition and selection. These techniques are generally known and do not need to be separately described here. The methods described herein may be implemented on various general or specific purpose computing systems. In certain embodiments, the methods of the present application may be implemented on a specifically configured personal computer or workstation. In other embodiments, the methods may be implemented on a general-purpose workstation, including one connected to a network. Alternatively or additionally, the methods of the invention may be, at least partially, implemented on a card for a network device or a general-purpose computing device. The processor/image processor may also include memory, storage devices, and other components generally known in the art and, therefore, they do not need to be described in detail here. The image processor could be used in conjunction with various manual, partially automated and fully automated (including robotic) hair transplantation systems and devices, including but not limited to systems for hair harvesting, or hair transplantation.

The imaging display device 140 may comprise a high resolution computer monitor which may optionally be a touch screen. The imaging display may allow images, such as video or still images, to be readable and for follicular units, and parts thereof, to be visualized. Alternatively, the imaging display device 140 can be other touch sensitive devices, including tablet, pocket PC, and other plasma screens. The touch screen may be used to modify the parameters of the hair transplantation procedure, directly through the image display device.

Methods, apparatus and systems consistent with the invention may be carried out by providing a modification interface, or user modification interface, including clickable icons, selection buttons in a menu, dialog box, or a roll-down window of an interface that may be provided to feed into the computer. According to another embodiment, the imaging display device 140 may display the selection window and a stylus or keyboard for entering a selection, for example, directly on the display itself. According to one embodiment, commands may be input via the modification interface through a programmable stylus, keyboard, mouse, speech processing system, laser pointer, touch screen, tablet computer, personal digital assistant (PDA), a remote input device (such as a pendant), or other input mechanism. The remote input device may include clickable icons, selection buttons, dialog boxes, or roll-down windows which are the same as or similar to those found on the user modification interface, providing a convenient way for the user to control common user interface functions from their position at the patient's side. Alternatively, the remote input device may only accommodate, for example, a subset of such modification controls, making for a more compact pendant. In yet another embodiment, the remote input device may be configured to accommodate additional modification controls. Moreover, either the remote input device or any other input mechanism may have icons which allow the user to control the robotic arm, allowing the user move the robotic arm away from the patient, or incorporate a STOP button, enabling the user to terminate operation of the robotic arm or hair transplantation tool in the event of an emergency. Alternatively, the modification interface may comprise a dedicated piece of hardware. In some embodiments the selections or adjustment made through the modification interface may be executed by code instructions that may be executed on the computer processor.

The program that runs the method and system may include a separate program code including a set of instructions for performing a desired operation or may include a plurality of modules that perform such sub-operations of an operation, or may be part of a single module of a larger program providing the operation. The modular construction facilitates adding, deleting, updating and/or amending the modules therein and/or features within the modules.

The program may include an electronic auditing function that enables capturing of selective data that is part of and contained within the apparatus or system. For example, the captured data may include a value of a parameter associated with the hair transplantation procedure, the apparatus or system carrying out the procedure, and/or the patient. The electronic auditing function may be configured in some embodiments to capture the individual steps or portions thereof that the system performs during the hair harvesting or hair implanting process of hair transplantation. The electronic auditing system may also be configured to capture parameter values associated with the hair transplantation procedure that are ascertained from the processing of the captured individual steps or portions thereof.

The program may receive unique identifier information and/or additional information and may access, for example, a storage device having data associated with the unique identifier information and/or additional information.

In some embodiments, a user may select a particular method or embodiment of this application, and the processor will run a program or algorithm associated with the selected method. For example, a user may select (e.g. by clicking and dragging, or clicking on a user interface icon, or by entering a command, a voice command, etc.) a hair harvesting program which includes operation of both sharp piercing needle and a duller coring needle. Alternatively the user may select to run a program controlling only a coring needle for a period of time to evaluate and adjust (if needed) one or more parameters of operation of a coring needle; or to run a program controlling only an implanting/site making needle to evaluate and adjust, for example, its depth of insertion or an angle.

A controller that may be operatively coupled to the processor may allow the speed, angle, and/or direction of a drive, as just an example, of the robotic tool (e.g., the hair harvesting tool) to be substantially automatically controlled. In certain embodiments, various types of position sensors may be used. For example, in certain embodiment, a non-optical encoder may be used where a voltage level or polarity may be adjusted as a function of encoder signal feedback to achieve a desired angle, speed, or force.

To aid in the understanding of the inventions of the present application, examples of the methodology will be described and explained in reference to the hair harvesting procedure. It will be apparent that the teachings can equally be applied to the hair implantation process, or to other appropriate processes with adaptations being made to accommodate the requirements of such process. To this end, before describing the hair harvesting procedure according to an embodiment of the invention, an example of the harvesting tool shall be described briefly to aid in the subsequent discussions.

Hair transplantation tools that can be used in a substantially automated, including robotic, system have been described, for example, in the commonly assigned U.S. Patent Publication No. 2008/0234699. In the case of a single sharp punch or needle being used for harvesting, sometimes if the sharp punch penetrates or punctures too deeply into the body surface, there is an increased chance that the follicular unit will be transected, thereby damaging it or rendering it unusable. Therefore, in some embodiments it may be desirable to use a hair harvesting or hair removal tool that comprises two concentric needles or punches, one of which is used to dissect deeper but is less sharp to decrease the chance of transecting follicular unit. In certain embodiments, an inside needle may be sharp or semi-sharp, and an outside needle may be relatively dull or less sharp than the inside needle. The inside needle may be used to initially pierce the skin and to form an incision, for example, of 0.5 mm to 2.0 mm deep. The outside needle can then follow the inside needle into the incision made by the inside needle and continue through deeper tissue to a depth of, for example, 5-8 mm. The relatively dull edge of the outside needle dissects the follicular unit separating it from the surrounding tissue and guides the follicular unit into the lumen of the outer needle without transecting or otherwise damaging the follicular unit. This enables removal or harvesting of the follicular unit while preserving its integrity. The outer needle body is sized and configured to at least partially surround or encapsulate a follicular unit. One or both of the inner and outer needles may be axially movable relative to one another, one or both of the inner and outer needles may also optionally rotate or oscillate. It is not required, however, for implementation of the inventions described herein that the inner needle be sharp and the outer needle be more dull, and it will be understood that in various embodiments the positions of these needles could be reversed, or various different configurations of the needles may be used, including the use of a single dissecting or harvesting needle (instead of two co-axial needles).

Figure 2A:
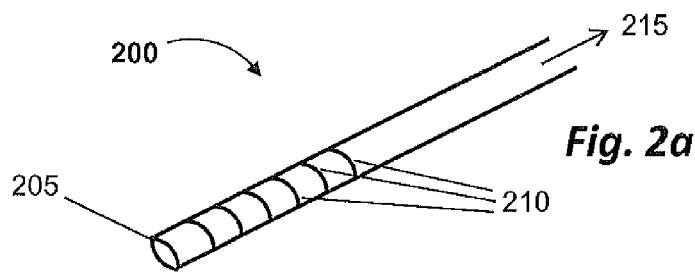
FIGS. 2a and 2b are examples of punches or needles that could be utilized in various embodiments of the inventions described herein.
Figure 2B:
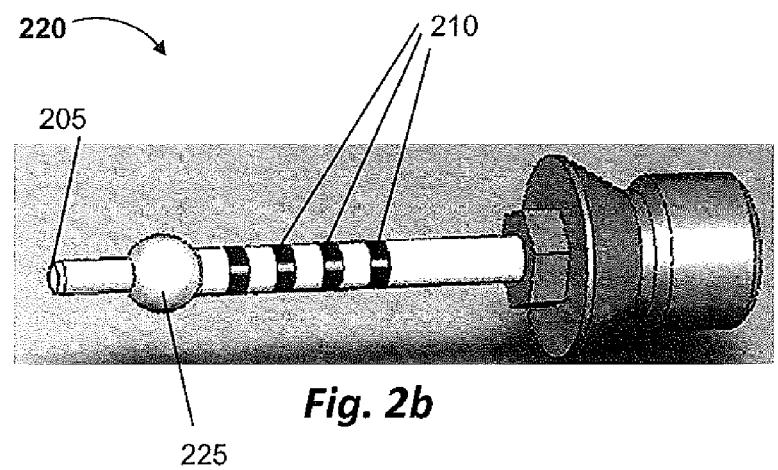

FIG. 2a illustrates an example of a distal portion of the needle or punch 200 that may be used in the harvesting tool. The punch 200 includes an elongated body having a sharp distal tip 205. The term "sharp" distal tip 205 as used herein means that it is sharp enough to pierce or cut a skin or body surface (not shown). The elongated body may be pushed into the skin such that its sharp distal tip cuts or penetrates tissue, or skin layers to a desired depth (e.g. through the epidermis, or upper dermis). A lower portion of the elongated body, the portion closer to the distal tip, may be provided with graduation markings 210 on its outer surface. Such markings assist in identifying the depth of insertion of the punch 200 in the body surface as explained in more detail later in reference to FIG. 3. The punch 220 represents an example of an alternative punch, for example, a dissecting needle that may be used in the embodiments implementing the two-needle configuration of the harvesting tool, or it could be a single-needle harvesting tool. Such punch 220 may include markings 210 and/or may also include a stop 225, as illustrated in FIG. 2(*b*). It will be appreciated that although the markings 210 have been illustrated and described herein as bands, the markings 210 may comprise any number of different shapes, forms or symbols and their format is not limited in this respect. The stop 225 is an example of a structure that limits the depth of insertion of the distal end of the punch 220 into the body surface. As the distal tip penetrates the body surface to the desired depth, the graduation markings provide a visual indication of the depth to which the distal tip 205 has entered the body surface. It will be appreciated that in some configurations where the stop is employed, the graduation markings may be disposed distally from the stop, both distally and proximally from the stop, or removed.

Having dissected the follicular unit from the surrounding tissue, the harvesting tool is withdrawn from the body or skin surface. Depending upon the particular configuration of harvesting tool utilized, the harvesting tool may be removed from the skin while a dissected follicular unit may still remain in the body surface, and then subsequently removed, for example, with the additional assistance of forceps, or vacuum, or other appropriate tools or mechanisms. Other harvesting tools are capable of dissecting the follicular unit and also removing it when the harvesting tool is removed from the skin. For example, a retention member (not shown) may be incorporated into the inner and/or outer needles of the harvesting tool to assist with the removal of the follicular unit.

The proximal end of the tool 200 may be configured to incorporate appropriate sleeves, slidable shafts, or other such structures to move the elongated body or bodies (needles/punches) axially and optionally radially relative to one another. In an alternative embodiment, the proximal end of the tool may be operatively connected to a mechanical system, electromechanical system, a pneumatic system, hydraulic system, or a magnetic system configured to effect controlled movement of the tool 200 (e.g., movement of the inner and outer needles relative to one another), and to facilitate a semi- or fully-automated tool to be employed. In yet another alternative embodiment, either or both of the inner and outer needles may be operatively coupled to a biasing mechanism, such as a spring mechanism, or other such release mechanism to facilitate movement of the needles in the axial direction, in a quick, or slow or otherwise controlled manner.

Figure 3:
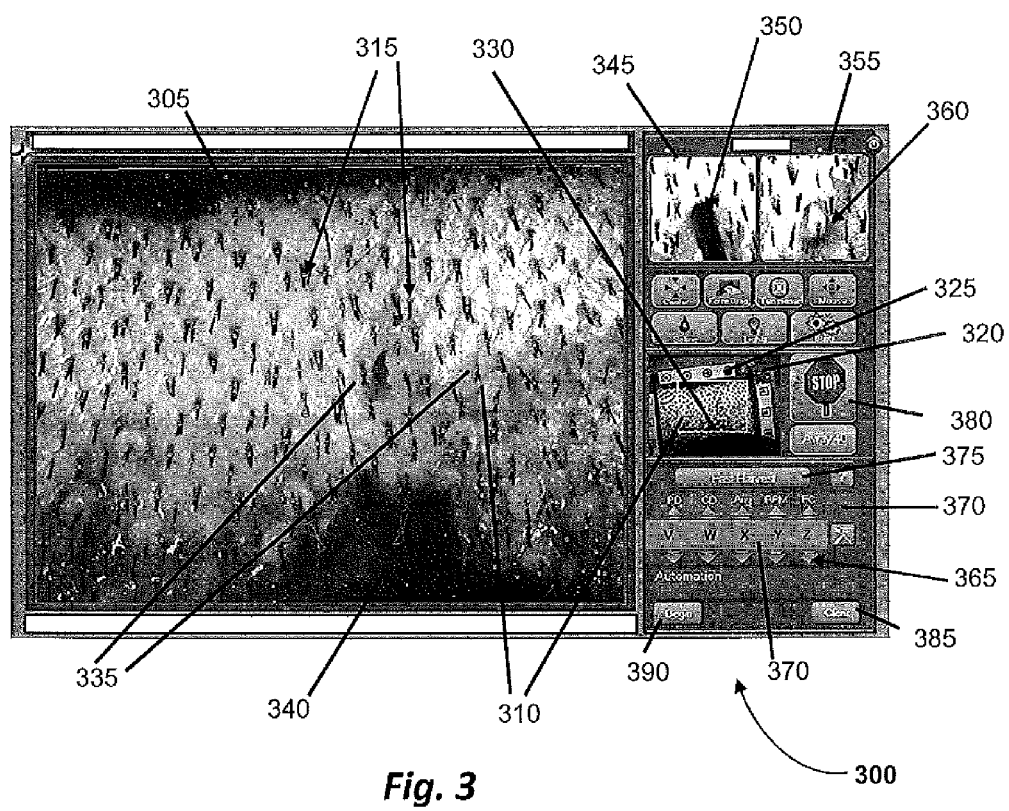
FIG. 3 is an example of a screen shot of a user display, which could be used to implement various embodiments of the invention.

FIG. 3 illustrates the view on an imaging display or monitor 300, which embodies several features of the invention, and facilitates validation or modification of parameters of an automated procedure, in this particular example a hair harvesting procedure. The monitor 300 shows several features, some or all of which may be utilized in various embodiments of the methods described herein, for example, in hair harvesting, hair removal, or hair implantation procedures. The monitor 300 includes a main section, which in the illustrated example takes up about two-thirds of the viewable space, and displays a real time image 305 of a body surface 310 which is undergoing a hair harvesting process. The real time image as used herein means an image that displays real time information captured by an image acquisition device, such as one or more cameras, for example, high-magnification camera(s) (such real time image is intended to include an image displayed, for example, with short delays of approximately up to 250 milliseconds, or in some examples from approximately 20 milliseconds to about 230 milliseconds). Some examples of the devices that could be used to obtain real time image include various cameras (e.g. webcam, surveillance cameras, linear cameras), or ultrasound sensing. In the streaming real time image, the user is able to see the individual follicular units 315 in the immediate area surrounding a currently being harvested (being removed, or being implanted) follicular unit, and operation of the tool as it is being inserted into and withdrawn from the skin. The monitor may also optionally display in addition to this large close up real time view 305, a more global view 320 (for example, using a pair of low-magnification cameras), that may appear on another section of the monitor 300 as a supplemental real-time image as seen in FIG. 3, this view displaying a real time image of the larger, for example, bound area from which the hairs are being harvested in this portion of the procedure. The tool bar of the user interface may allow the user to select which view or views to display (stereo, high-magnification, or low-magnification, etc.) For convenience of the description, dissecting or harvesting of a single follicular unit (which may comprise one or more hair follicles) will be referred to as a harvesting event, and implanting of a single follicular unit will be referred to as an implantation event. For other procedures where present inventions may be implemented, the relevant event may be, for example, a tissue removal or tissue cutting, ablation, dermatologic, ophthalmic, or a tattoo removal event. Optionally, fiducials or markers 325 shown in the global view 320 can be placed, for example, directly onto the body surface, or may be attached to a skin tensioner that may be used in the hair transplantation procedure or other appropriate procedure where skin tensioning is desired. In this more global view 320, a virtual box 330 is identified, this box corresponding to the region of the body surface that is shown in the real time image 305. In this manner, with the concurrent showing of the main real time image 305 and the global real time view 320, the user is able to obtain an overall view and better understanding of from where follicular units still need to be harvested, from where follicular units have already been harvested, and be generally informed of issues that may be arising as the procedure continues. An example of an issue that might be arising for example, is that the tool may be operating off-center, that is actually centering at a point different to the targeted point of the follicular unit instructed by the processor and/or control unit; or perhaps the user may be noticing an increase in the transection rate of the dissected/harvested follicular units. The apparatus, system and methods of this application, enable the user or the automated apparatus/system itself, or a combination of the above to utilize the information displayed, such that the parameters of the procedure during at least a portion of the procedure may be validated or modified, if warranted, and that it may be done without having to necessarily interrupt the procedure, or interrupt it for a significant time.

As illustrated in FIG. 3, the visual representation of the real-time information may be combined using known image processing techniques, for example, with a virtual representation 335 of the location from where follicular units have been harvested. Such virtual representation will assist in differentiating the already dissected follicular units, for example, by forming a colored circle or other configuration around dissected/harvested follicular unit to more clearly visually represent that harvesting has occurred in that region. The examples of various virtual representations are described in a commonly assigned application Ser. No.

13/174,721 and entitled "Methods and Systems for Directing Movement of a Tool in Hair Transplantation Procedures." The color selection of the above visual representations may be such that these already harvested regions can be more easily differentiated, for example, from the area of blood 340 that also may be seen in the image 305. In other embodiments, for example, the real time image may be combined with a virtual representation of the location from where follicular units have been already implanted.

The streaming real time images 305 are useful in making certain decisions, for example, where a user needs to override an automated selection of the next follicular unit to be harvested that is made by the system. For example, by observing automated operation, the user may want to avoid an area where hair grafts were already harvested or avoid harvesting areas near scars or any other undesirable harvest sites, and therefore, needs to override on the spot a selection made automatically by the system in such area. In other situations, because the automated operation of the tool may be too fast, streaming of real time images may result in an insufficient time for the user to observe certain parameters and timely made an appropriate decision. Therefore, in addition to the main real time image 305 (and optionally the global real time view 320), one or more supplemental snapshots or images, as described below, may be also provided concurrently. In FIG. 3, by way of example two additional supplemental images/snapshots are shown, each of the snapshots taken at a different moment in time during the streaming of the real time images, but relating to the same follicular unit that is being harvested, or the same harvesting event. In other words, such snapshots, even though are based on the real time imaging, are not the real time images, but rather represent historic information of a state of the procedure at a particular moment or interval in time during streaming of the real time images. In this particular example, each of the first supplemental image 345 and the second supplemental image 355 is a still image. However, instead of a still image, in some embodiments snapshots 345 and 355 may be videos, for example, short videos of 0.5 to 3 seconds duration, or it may be simply a recording of the previously taken real time images that is run or looping in a slow motion or pace (e.g. less than 30 frames per second) to allow the user to observe the details and identify whether any adjustments are desired or warranted. The first supplemental image 345 may be captured, for example, when the harvesting needle 350 penetrated or punctured the body surface to a maximum designated depth of penetration and the skin has substantially stabilized, recovered, or settled from the rapid action of the harvesting needle, or at a predetermined time interval after activation of the needle, for example a tenth of a second later. If a punch 200 with graduation markings 210 is utilized, the user will be able to see how deep into the body surface the punch 200 has penetrated in this first supplemental image 345. With the correct magnification, the user will be able to at least see the various markings, and ascertain the approximate length of the inner needle or punch 200 that has penetrated the body surface. Alternatively, an electronic auditing function in the program associated with the harvesting procedure may be configured to capture quantitative information, a value pertaining to the depth of insertion of the punch 200, and perhaps retain that information in memory for later retrieval or use.

The second supplemental image 355 may be captured at an instance when the harvesting event, such as the dissection of a follicular unit, is substantially complete. Typically, it would happen once a distal tip of the harvesting needle has been retracted from the body surface. For example, in the case of a two co-axial needle configuration, the image may be captured at a time when both the inner and outer needles have been retracted from the body surface, or a predetermined time after the second of the two needles is removed. One of the benefits of having this second supplemental image 355 is that the user can observe if, and optionally how, the follicular unit is being elevated from the body surface. For example, if the follicular unit or a portion of it is seen lying on the surface in unusual orientation, it may be an indication that follicular unit was transected during harvesting. On the other hand, if the follicular unit appears to be at least partially elevated from the surface, this may be an indication that dissection was successful, and the follicular unit is now ready to be removed from the body surface, for example, by forceps or some other means. In addition, the user may be able to observe an image 360 of the incision made around the follicular unit, and may be able to ascertain if the harvested follicular unit was centered with respect to image 360 of the incision, or if the harvesting tool operated off-center with respect to the targeted follicular unit. Alternatively, an assessment of the centering of the tool may be accomplished automatically. For example, an electronic auditing function in the program associated with the harvesting procedure, may be configured to capture quantitative information, a value pertaining to the amount that the follicular unit is offset from the center of the image 360, and perhaps retain that information in memory for later retrieval or use.

While the first and second supplemental images 345 and 355 are displayed as essentially historical information pertaining to harvesting of a particular hair follicular unit, the real time image 305 and the more global real time image 320 continue to display real-time imaging of the ongoing follicular unit harvesting process. For each event, that is for each follicular unit harvesting attempt, a supplemental image set (that may comprise simply one supplemental snapshot, such as image 345, or any desirable number of the supplemental snapshot images, for example 3, 4, or 5 snapshots) may be captured. In the example of FIG. 3, for each follicular unit harvest attempt, a first supplemental image 345 and a second supplemental image 355 is captured, providing a record of information pertaining to the depth the punch needle 200 penetrated the body surface, the angle of the needle, and also the quality of the harvested follicular unit and/or the quality of the harvesting procedure.

When viewing the first supplemental image 345, should the user recognize a deviation from expectation or desire, for example, should it be identified that the depth of penetration is too deep, the user has the opportunity to reduce the penetration depth. If the penetration depth is too deep, the incision may cut through the epidermis and dermis into the subcutaneous fat. A typical pattern of damage to the hair follicle that may result from the penetration depth of the punch 200 being too deep is a transection in the upper portion of the hair follicle. Should the user become aware of this problem, he may, for example, by using his mouse to click on an arrow 365 on the panel 370, which is associated with the penetration or puncture depth (PD) of the punch 200. Once the user clicks this arrow 365, the value V associated with the puncture depth (PD) is modified, and the program of the computer is able to execute that instruction, communicating that modification to the controller such that the puncture depth PD of the punch 200 is modified. Depending upon the time it takes for the program to carry out this modification request (or based on a specific setting of the delay in implementing the modification), the next follicular unit harvest attempt may be carried out at this modified penetration or puncture depth PD, or alternatively, the modified puncture depth PD may be applied to a subsequent attempt. Likewise, if the user should recognize or identify that the depth of penetration or puncture is too shallow, he may choose to increase the penetration depth utilizing the appropriately programmed arrow on the panel 370, which will similarly provide the necessary instructions to the control unit such that the penetration depth is increased. In some embodiments, instead of the arrow on the panel 370, the user may use a corresponding arrow or button of the remote control input device. In this manner, the user is given the opportunity to modify the value of a parameter if it is found to be not optimal, less desirable, or outside one or more acceptable limits, during a session of an automated hair transplantation procedure, without having to necessarily stop the harvesting procedure. It will be appreciated that although it may not perhaps be necessary to stop the harvesting procedure, it may be desirable from either the user's perspective and/or the system's perspective (depending upon the nature of the program and the related software and hardware configuration(s)), that the system be at least paused so that user has a longer opportunity to view the first supplemental image 345 and/or to make the necessary change(s) to the system. Once the modification has been carried out, the user may then re-start the procedure, enabling the modification to be executed. The user will have the opportunity to view a first supplemental image 345 associated with the modified penetration or puncture depth, and ensure that the modification was sufficient for his/her purposes. If not, further modification can be requested in a similar manner. Alternatively, the imaging processing may be utilized to automatically identify whether a modification of puncture depth is required. For example, the system may be configured to take a snapshot or first supplemental image 345 at an instant indicative of the maximum penetration depth after the skin has settled. The image processor may be configured to automatically identify (without input from the user) the markings on the punch, and to identify where the body surface is with respect to the markings. Such identification may be based on captured data, and not on an actual "visual image". For example, if it has been predetermined that there should be three markings on the punch that are visible above the skin surface, but only two such marking are identified by the image processing, based on these findings, the processor may be configured or programmed to automatically modify the puncture depth accordingly. It could be modified, for example, to ensure that subsequent punching of the body surface by the harvesting tool results in three markings being seen in a future supplemental image, such as image 345. In the above example, the processor may automatically reduce the penetration/puncture depth by an amount substantially equivalent to the spacing between the second and third markings or as otherwise necessary to ensure the desired result (in this case visibility of the three markings) is attained. It will be appreciated by those skilled in the art that there are various methods by which the processor may be configured to automatically carry out a "visual" inspection of the "image", such that the system may automatically modify, for example, how deep a punch or needle penetrates the body to enhance the system's performance. One such method is described herein, though there are numerous variations and alternatives that may be utilized to accomplish the same or similar goals. With reference to the example of FIG. 2a, the needle or punch 200 comprises a portion with graduation band markings 210 thereon, which provide a visual indication of the depth to which the distal tip 205 of the needle has entered the body surface or tissue. Various numbers of graduation markings may be coated on the needle or punch 200.

As mentioned above, the supplemental image 345 capturing the puncture depth is taken. This image may be enhanced, if needed, to provide a clean and crisp image. Such image enhancement may comprise using a number of filters, such as a sharpen filter, histogram equalization, gamma correction and pseudo color mapping.

The method may begin with processing the punch or needle image to find an axis of the needle. This processing can be carried out manually, or by calibration, a calibration typically providing for the needle tip 205 and the axis in the direction 215 to the proximal end of the needle to be identified. Having ascertained the axis of the needle, an intensity profile of the needle image is generated along the axis, which is in the direction 215. The intensity profile is typically a measurement of intensity variation of image pixels, along the length of the needle 200. The intensity measurement may comprise evaluating the actual intensity level of a pixel, or merely evaluating whether the intensity of a pixel is above or below a certain threshold, thereby facilitating a binary value, for example, to be assigned to the pixel. In this manner, the intensity profile identifies the transition to and from graduation markings on the outer surface of the punch or needle 200. In an attempt to reduce errors in the intensity measurement, rather than just evaluate the intensity of single pixel in the image, optionally the intensity of two or more pixels in a direction substantially orthogonal to the direction 215 may be measured, and a mean value of the two or more pixels calculated, and the standard deviation along the profile may be calculated. From the mean value of the intensity calculated, and the standard deviation along the profile, the profile can be segmented and the graduation marks on the outer surface of the punch or needle identified. The number of pixels used in this calculation may vary, the optimum number being that which provides the best solution, for example, a number may vary between 3 and 10 for various applications, or (since the band markings may be placed around circumference of the tool) it may be the number of pixels that provides for coverage of up to approximately 50% of the diameter of the tool. Optionally, in the event that a stereovision imaging system has been utilized, consistency of the results from the left and right images can be measured, providing for a means to remove unpaired marks and confirm the presence of graduation marks by the presence of a mark in both left and right images.

Figure 2C:
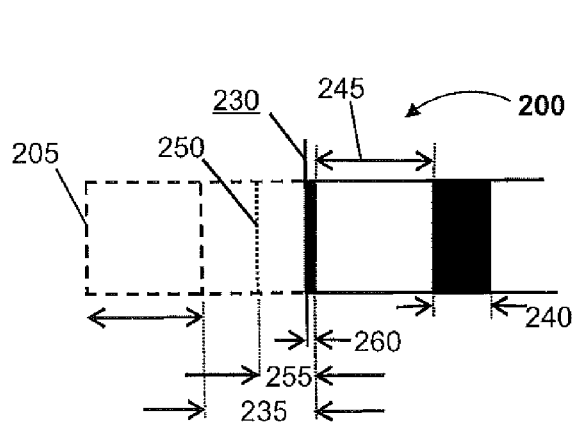
FIG. 2c illustrates schematically an enlarged portion of a needle or punch with band markings.

In some embodiments, it may also be possible to modify the manner in which these intensity values are calculated or to tune the results achieved to better match prior knowledge or expectations. For example, the width of the markings may be fine-tuned, scaling the width of markings to meet prior knowledge, such as the known design of the graduation markings, as illustrated in the example of FIG. 2c. In this example, the needle 200 is shown schematically penetrating a body surface 230, solid lines representing elements above the body surface 230, and broken lines representing elements that are beneath the body surface, and therefore not usually visible to the user. The design of the graduation band markings in the example shown is as follows. The first marking begins at a location, for example, 0.5 to 2 mm from the needle tip 205 and it has a width 235 of 1 mm; the second marking has a width 240 which is 0.5 mm, and the first and the second markings are separated from each other by a distance 245, for example, of 1.0 mm. The placement of the first marking, the number of the markings and the width of each marking, as well as the distances between the markings are provided above by way of an example only. For example, in some embodiments, the width of each marking may be the same, or different; the distance between various markings may be the same or different; and the location of the first marking may vary depending on the procedure and particular implementation. Armed with this prior knowledge, the images acquired can be processed, and appropriate corrections and calculations carried out on the intensity profile to provide the user and/or the system with an indication of the number of full or partial graduation marks that are on the needle and above the body surface. Knowing how the actual design of the graduation marks on the needle correlates to the image of the graduation marks on the needle, may also enable the processor to compute the width of any partial dark band 210 or the width of any partial separation 245 that lies just above the body surface. In this manner, the system can determine whether the needle has penetrated the body surface to the desired depth, or whether a greater or lesser penetration depth into the body surface is required. In a fully automated system, the system can utilize the information gained on the full or partial graduation marks above the body surface, together with the knowledge of actual physical distances they represent to provide the necessary instructions for the needle puncture depth, and to adjust it if necessary to be the same, a greater or a lesser depth for the next or a subsequent needle puncture.

For example, with reference to FIG. 2c, assume that a desirable needle penetration is achieved when the width of approximately half of the first marking can be seen above the surface 230. With reference to FIG. 2c, that would be a width of 0.5 mm (255) which represents one half of the full width 235 of the first dark band 210, and this portion of the dark band 210 down to the dotted line 250 would have to be located above the body/skin surface 230 and be visible. However, as seen in the example of FIG. 2c, after initial penetration of the needle only a small portion 260 of the width of the first dark band 210 is visible above the surface 230. Therefore, it indicates that the tool punctured the tissue deeper than the desired depth. Based on these findings, which may be ascertained via the supplemental image 345 from which the captured puncture depth was taken, the penetration depth of the needle 200 can be adjusted such that the needle 200 penetrates the body surface 230 to a lesser depth to make a desired half of the first marking visible above the surface 230. In some embodiments the adjustments may be made available in one or more increments, for example, a small adjustment of 0.1 mm and a larger adjustment of 0.25 mm. It will be understood by those skilled in the art that any number of adjustments in any desired increments (or continuous adjustment) may be implemented. According to the results from the image processing, different feedback adjustment policies may be implemented and applied. In the example of FIG. 2c, a complete second marking is visible and instead of the desired visible portion of 0.5 mm (255) of the first marking, only about 0.1 mm portion (260) of that marking is visible above the surface (a 0.4 mm difference). In light of the above, the system is able to determine that only a relatively small adjustment may be needed to decrease the depth of the tool puncture and can be configured to automatically adjust the depth accordingly, and also optionally to operate the needle to puncture at the reduced adjusted depth. In a different situation, where on initial penetration only the second dark band 210 were visible, it would be apparent that the penetration depth would need to be reduced by a greater amount, and a larger adjustment would need to be applied. In some embodiments, the processor may be configured such that if an absolute difference between the desired value of the visible mark and the actual measured value is equal or less than a certain predetermined value, then a small incremental adjustment (for example, of 0.1 mm) shall be automatically made in an appropriate direction of increase or decrease of the depth. In some instances, if the difference is relatively small or insignificant for a particular application, no adjustment may be implemented. Similarly, the processor may be configured such that if the difference between the desired value of the visible mark and the actual measured value is more than a certain predetermined value, then a larger incremental adjustment (for example, 0.25 mm or 0.5 mm) shall be automatically made. It will be appreciated that due to the skin elasticity and often non-linear response to pressure, there may not necessarily be a 1:1 correlation between the required penetration depth adjustment and the measured or viewed difference between the desired and actual visible widths of graduation markings. This will vary on the nature of the body surface, for example the type, age, location and condition of the body surface, and other factors. In the example given, even though a 0.4 mm difference is illustrated in FIG. 2c, the actual needle adjustment may only need to be, for example, 0.2 mm for the desired portion 255 of the first dark band to be disposed above the body surface.

Figure 2D:
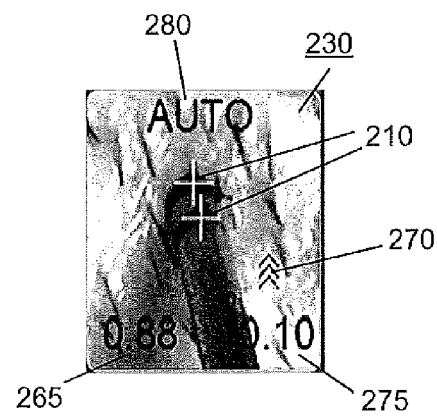
FIG. 2d is an example of a supplemental image that may be incorporated into the user interface or display.

The above has described some examples of the automated embodiments in which the image processing is able to provide the required information necessary to enable the needle penetration depth to be automatically adjusted. In other embodiments, the information available to the user via images, for example the supplemental image 345, can enable the user to adjust the penetration depth him/herself. In some embodiments an image such as that illustrated in FIG. 2(d) can be incorporated into a supplemental image 345. This image may serve to display to the user, the graduation markings or dark bands 210, thus enabling the user to make his/her own determination if needle penetration depth adjustment is warranted. If adjustment is desired, the user may use any suitable interface to effect adjustment. Also, with an additional optional display as shown in FIG. 2d the user may be shown, for example, by 265 the value of the actual visible width of a first distal marking, by an arrow 270 a direction in which any adjustment is currently being made or needs to be made, and by 275 the value of the depth adjustment being made or needed. Moreover, in some embodiments, an indicator 280 AUTO may inform the user whether the adjustments are being made automatically by the system, or perhaps the system operates in the manual mode MAN (not shown) enabling the user to control the needle penetration depth manually. A user interface may facilitate adjustment of any or all of the parameters referenced above.

Figure 2E:
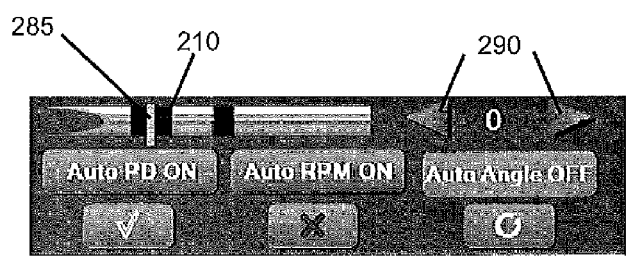
FIG. 2e is an example of a portion of a user interface that may be incorporated into the user display.

Alternatively, or in addition, visual means such as that illustrated in FIG. 2(e) may be employed. In this particular embodiment, the user is not required to know the actual value of the penetration depth or the amount by which it should be adjusted, but can indicate the adjustment by moving the bar 285 on a schematic representation of the needle, in the appropriate direction to the desired position. In this instance, for example, the bar may be representative of the body surface, so placing the bar 285 substantially in the middle of the first dark band 210, will indicate that the user desires that the needle puncture depth must be such that substantially half of the first dark band 210 is visible above the body surface. Alternatively, or in addition, the arrows 290 may be utilized to move the bar 285. The schematic representation of the needle and the movable bar for depth indication may be incorporated, for example, into the bottom right portion of the user interface shown in reference to FIG. 3.

Although it is possible for each and every penetration or puncture depth to be adjusted individually, it may be more efficient to control and only periodically adjust the tool puncture depth based, for example, on the location of the next puncture relative to the previous puncture and/or on the prior knowledge of the previous adjustments made in various areas of the body surface. For example, the penetration or puncture depth adjustment applied to the current harvest may also be applied to the next or a future harvests. For example, if the next follicular unit to be harvested is located in close proximity (for example, within 5 mm) of the follicular unit currently being harvested, a system may be configured to apply substantially the same penetration depth to the next follicular unit. If the next follicular unit to be harvested is far away from the follicular unit currently being harvested (for example, greater than 5 mm), the penetration depth may be adjusted as needed for that follicular unit. However, in some embodiments, the specific prior penetration depths and adjustments employed to harvest follicular units from the various locations on the body surface, can be stored by the system, and this historic information may be utilized for future harvests. In this instance, if it is desired to move a tool to a new location from which at least some follicular units were already previously harvested, the system can use a stored penetration depth and relevant adjustment information for these one or more previous harvests, or in some embodiments may calculate an average of those penetration depths and adjustments in a particular area, such that further automation may be realized in a more efficient manner.

In the manner of the examples described above, the system is able to automatically carry out a "visual" inspection of the "image" and automatically modify one or more parameters (in this instance is the depth of penetration or puncture) to enhance the system's performance. It will be appreciated that examples and embodiments discussed herein with reference to the modification of the puncture or penetration depth of the tool are applicable to various procedures. For example, in reference to hair transplantation, they are applicable to not only dissection or harvesting of hair (as referenced above), but to the implantation site creation procedure and/or the hair implantation procedure itself. In other applications, automatic modification of the penetration depth may be applied to various aspects of the corresponding procedures.

Similar modification can be carried out pertaining to other parameters associated with the hair harvesting procedure, or other procedures within the scope of the inventions described herein. For example, another parameter that may benefit from an automated or semi-automated modification is an angle or orientation of the tool used in the procedure. As described in detail in the commonly assigned U.S. Pat. No. 8,048,090 (which description is incorporated by reference herein) the hair direction or angle changes substantially below the skin as compared to that of the above the skin. It has been observed that an emergence angle of the hair follicle from the skin is quite often smaller/more acute than its subcutaneous course, however, in some instances it may be the other way around. It should be noted that the description based on the hair transplantation example refers to follicular units, which are naturally occurring aggregates of one or more hair follicles (typically, 1 to 4). While each hair follicle within a follicular unit typically has its own axis and direction above and below the skin surface, for simplicity we will refer to the axis of the follicular unit as a whole (which would represent an average or mean axis of visible portions of all hair follicles in the follicular unit). As a result, aligning a tool (for example, hair harvesting tool) with a visible axis of the follicular unit above the skin and advancing the tool based on the visible portion of the hair above the skin may result in follicular unit transection, damaging it or rendering it unusable. Therefore, it is important to determine an emergence angle of hair from a body surface (e.g., scalp, skin) as well as determine the proper tool orientation relative to the body surface, which is referred to as "approach angle of the tool." With reference to the hair transplantation procedures, the proper tool orientation is important in both harvesting of hair and implantation. The correct angle of the tool orientation reduces the transection rates during harvesting, it also prevents the tool (harvesting or implanting needle, or site making tool) from sliding on a surface, scraping the skin or tissue, or insufficiently penetrating the body/skin due to unnecessary small angles at which the tool (e.g., needle) may approach the surface. Further, during implantation, correct angle of the tool allows to properly match the angles of the existing hair so that newly implanted follicular units blend in more naturally.

It will be appreciated by those skilled in the art that there are various methods by which the processor may be configured to automatically or semi-automatically modify the value of the angle of the tool parameter. Several examples of such methods are described herein, though there are numerous variations and alternatives that may be utilized to accomplish the same or similar goals. According to one approach, the following method of automation of an angle clamp may be implemented as will be described in reference to FIG. 5. It will appreciated that though discussed in terms of hair transplantation, orientation of the tool may comprise orienting a tool for various applications.

Based on various factors and certain characteristics, including one or more of prior or existing data, experience, characteristics of the follicular units, characteristics of the body surface or area in which the follicular units reside, the geometry and design of the tool or mechanism used in the procedure, the force required to facilitate a desired skin surface penetration, the dimensions of any skin tensioner that may be utilized in the procedure, measurements of the emergence angles or the average/mean emergence angles of the existing hair in the relevant area, it was determined that there exists a cut-off tool approach angle (also referred to as minimum approach angle of a tool or an angle clamp) below which the tool shall not be oriented, for example, below which the tool shall not be aligned with the relevant follicular unit. The value of a minimum approach angle can be determined, for example, for a particular area on the body surface. For example, the minimum approach angle at the top of the scalp may be different to the minimum approach angle at the sides or the back of the scalp. Different minimum approach angles may be chosen depending on a particular follicular unit and its emergence angle, or based on the desired angles of the "virtual hairs", for example, when planning hair implantation. Typically, the smaller the emergence angle of a particular follicular unit, the greater the difference between the emergence angle of this follicular unit and a minimum tool approach angle.

By examining closely the hairs in a relatively small area, for example, of the scalp or another body surface, it was observed that follicular units might not be pointing exactly in the same direction. Therefore, it may be beneficial to average an emergence angle of follicular units in a selected neighborhood (e.g., 100 hair graft or more; visible hair on a screen of a user display, or within 25 mm radius of a selected follicular unit, etc.). Averaging eliminates individual noise, hairstyling difference, or with reference to the robotic systems it increases the speed and efficiency of the procedure because it requires less reorientation and movement of the tool. Therefore, in some embodiments, the determination of the minimum approach angle may be based on the average or mean value of emergence angles of a plurality of the existing hair in the particular relevant area. No matter how the minimum approach angle is determined, while it will work properly for most follicular units in that particular area, it may still not be suitable to use with a particular follicular unit. For example, it may not work for a certain follicular unit located within the relevant area whose emergence angle is substantially different than the determined average emergence angle for the follicular units in that area. For such follicular unit, it may be desirable to adjust the suggested default minimum approach angle. For example, if the emergence angle of the follicular unit of interest (e.g., one that is intended to be harvested) is less than a pre-selected minimum approach angle, it may be desirable to orient the tool at the minimum approach angle, rather than the emergence angle of the follicular unit. If the emergence angle of the follicular unit of interest is greater than or equal to the minimum approach angle, it may be desirable to orient the tool substantially to the emergence angle of the follicular unit of interest. However, it has been found that often, it is desirable that the approach angle of the tool be different from the emergence angle of the follicular unit of interest. In certain applications and depending on a particular follicular unit and/or its location, it may be desirable, for the reasons mentioned above, to add approximately as much as 15°-25° to the emergence angle of the particular hair follicle or follicular unit to determine a desirable minimum approach angle. For example, if the hair emergence angle is 35°, a minimum approach angle of about 50° to 55° may be used to produce acceptable harvesting results. However, if the actual emergence angles of follicular units on a particular patient are relatively high, then the difference between the average emergence angle and the minimum approach angle may be set to be smaller, for example, only 10°.

In one embodiment, the following logic for the angle adjustment may be implemented. The current minimum approach angle is compared to the emergence angle of the follicular unit of interest and the following logic may be applied based on the results of such comparison:

a) If the current minimum approach angle is greater than the emergence angle of the follicular unit of interest, then the current minimum approach angle may be used as the actual tool approach angle for that particular follicular unit. However, as an example, the following modification may be super-imposed on this initial logic. For example, if the difference between the minimum approach angle and the emergence angle of the follicular unit of interest is less than a selected number of degrees (e.g., 5° or 10°), it may be desirable to choose a tool approach angle which is substantially equal to the sum of the selected number of degrees and the emergence angle of the follicular unit of interest.

b) If the current minimum approach angle is the same or lower than the emergence angle of the follicular unit of interest, then the emergence angle of the follicular unit of interest may be used as the tool approach angle. However, again the following modification may be super-imposed on this initial logic. For example, it may be desirable to choose the tool approach angle which is substantially equal to the sum of the selected number of degrees and the emergence angle of the follicular unit of interest. In another example, if the emergence angle of the follicular unit of interest is greater than the minimum approach angle by more than a predetermined value, the tool may be oriented to an angle not more than a sum of the minimum approach angle and the predetermined value, and above the minimum approach angle.

Below are some examples of the above implementations. Assume that the user desires that a difference between the emergence angle of any particular follicular unit and the actual tool approach angle should be always at least 5°. In this case, if the angle clamp is set at 55° and a particular follicular unit has a slightly lower emergence angle of 52° (the difference between the two angles is less than 5°), then the tool approach angle will be automatically set by the system at 57° (52°+5°=57°). Alternatively, if the angle clamp is the same (55°) but a particular FU has a higher emergence angle (e.g. 58°), then the tool approach angle will be automatically set by the system at 63° (58°+5°=63°).

The methods and systems described herein allow for automatic or semi-automatic selection and changing of the angle of the tool parameter. According to one approach, the following method of automation of the angle clamp may be implemented as will be described in reference to FIG. 5.

Figure 5:
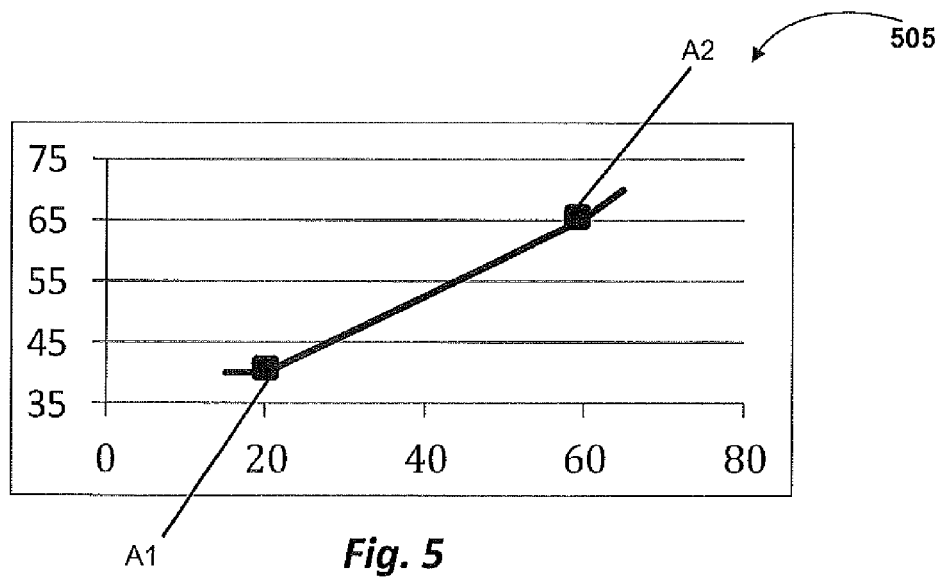
FIG. 5 is an example of the graph representing one embodiment of the methodology for determining angle clamps for the representative emergence angles of follicular units.

FIG. 5 illustrates a graphical representation of the proposed angle clamps (minimum tool approach angles) corresponding to a particular average emergence angle of follicular units. This graph 505 demonstrates how to choose automatically a default angle clamp for the corresponding emergence angle of the follicular unit and it may be built according to the following method. The user or the processor (for example, based on stored information, statistical data, or otherwise), selects a first minimum approach angle A1 (at 40°) which corresponds to an average emergence angle of a plurality of follicular units with a first relatively shallow emergence angle (e.g., 20°), and a second minimum approach angle A2 (at 65°) which corresponds to an average emergence angle of another plurality of follicular units with a second relatively high emergence angle (e.g., 60°). The processor may interpolate, in this example linearly, between these two values A1 and A2, creating the graph 505 which provides suggested minimum approach angles for the average emergence angles of follicular units that lie between the first and the second minimum approach angles, 20° and 60° respectively. This interpolation, although shown to be linear in the example of FIG. 5, may be quadratic, cubic or any other type or combination of types of interpolation, and instead of two points A1 and A2, an angle associated with an upper average or mean emergence angle and an angle associated with a lower average or mean emergence angle, or a different number of the initial points may be selected. These minimum approach angles may be user-specified or based on historic data. Further, additional adjustments to the proposed minimum approach angle of the default graph may be implemented if desired. For example, the proposed minimum approach angle may be increased or decreased by a particular number of degrees and this adjustment may be super-imposed on the automated calculation of the default angles clamps. Having created this graphical representation, the processor is able to find the associated minimum approach angle for any follicular unit average emergence angle, and use that value when comparing the emergence angle of the actual follicular unit of interest. Based on the comparison of the values, the processor can then automatically or semi-automatically change the angle of the tool parameter, and even instruct the corresponding tool orientation in certain implementations. If the orientation is not to the user's liking, he/she may modify the orientation or the graphical representation to meet his/her needs.

According to the inventions described herein, the minimum approach angle or the angle clamp may be chosen automatically for a wide variety of patients with an understanding that these patients may have a wide variety of follicular unit emergence angles in various areas, of the scalp or other body surface. For example, on the same patient, depending on the location of the follicular unit, the follicular unit emergence angle may vary from low angles below 25 degrees to the relatively high angles of 60 degrees and even more. Nevertheless, any automated algorithm, including the one described above, however widely applicable it may be, may not work in some special cases, and therefore, would need to be adjusted. Such adjustment of the default automation algorithm may be accomplished, for example, in the following different ways.

According to one implementation, the system may allow to switch from an automatic minimum approach angle calculation to a manual mode, and back to the automated mode. For example, the user may elect to temporarily or permanently terminate the program responsible for automatically determining the angle clamp, (or automatically orientating the tool), and switch to manual selection, where the user selects the angle at which the tool will be oriented, or alternatively, an angle clamp, for example, as it penetrates the body surface to harvest the follicular unit of interest. According to another implementation, the user may interactively adjust the above described default automation algorithm. In this embodiment the user may be provided with a user interface via which he/she may modify the orientation of the tool directly or indirectly. For example, the user interface may comprise a graphical representation in which a plot of average follicular unit emergence angle against minimum tool approach angle is illustrated, and the user may interactively adjust one or more values on the graphical representation, which is turn adjusts operation of the tool orientation. This implementation will require computer-savvy advanced users. Alternatively, according to yet further implementation, a combination of the manual and automated adjustment may be implemented as described below. Specifically, an adjustment of the automation algorithm may be based on user input for a specific follicular unit as will be described in reference to FIG. 6.

According to one implementation, the user input could adjust, for example, one proposed angle clamp that is closest to one of the points used in the interpolation (e.g., points A1 or A2 of FIG. 5), while keeping the rest the same or appropriately adjusted. In one embodiment, the user may desire that the minimum approach angle for a particular selected follicular unit be changed such that based on this input the graph of FIG. 5 is adjusted, and then the system continues to provide automation of this parameter. A typical user input with respect to a particular follicular unit will be one of the following two:

1. Minimum approach angle (angle clamp) needs to be smaller or more shallow for the specific follicular unit, or 2. Minimum approach angle needs to be higher for the specific follicular unit.

Figure 6:
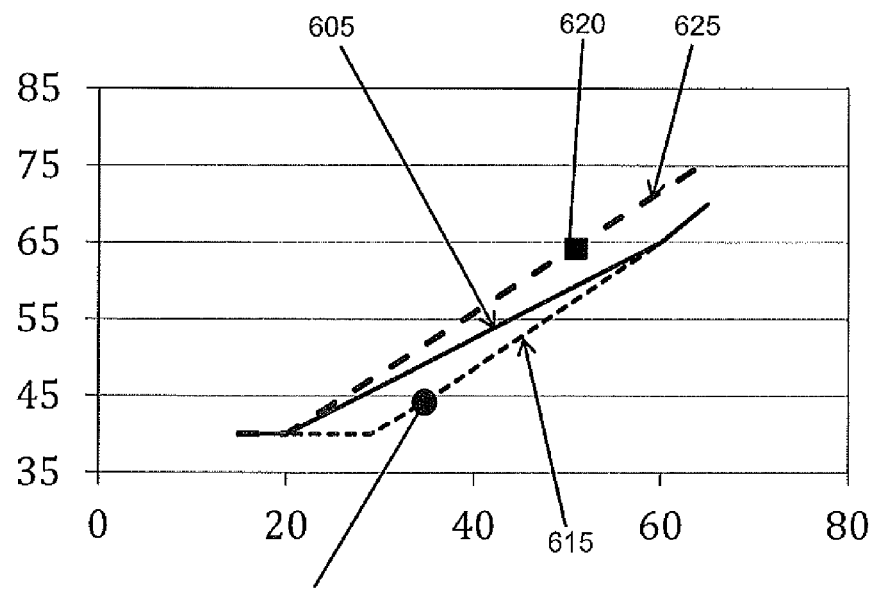
FIG. 6 is an example of the method for modifying the graph of FIG. 5.

Both of these situations may be handled in a similar manner. When a user wants the angle clamp for a particular follicular unit to be smaller/more acute/more shallow, it generally means that the angle clamp needs to be decreased for this specific follicular unit by a small amount (e.g., five degrees), and for all other follicular units the system may automatically decrement the angle clamp by an appropriate amount and reconstruct the graph accordingly. This is illustrated in FIG. 6, where a default solid line 605 represents a graph of suggested minimum approach angles for a range of average emergence angles of follicular units, the default graph 605 created for example, as described in reference to FIG. 5. Let's say the user provides input for follicular unit having the emergence angles of 35° to be more acute/shallow than the default, for example, by 5°, as illustrated by a point 610 in FIG. 6. The point 610 that now represents a new adjusted minimum approach angle (45° instead of the default 50° in this example) for the follicular units with the emergence angle of 35°. The user may utilize the user interface or remote control to input the change for a point 610, or it may instruct the system to subtract (in this example) a few degrees from the default value. Of course, in other examples, instead of subtracting the user may increase the default value by adding a desired number of degrees, or simply by dragging the point of interest on the graph, or by any other appropriate means. The processor is then able to automatically adjust other minimum approach angles and reconstruct the graph based on this new adjusted point 610 and by keeping the original default 65° angle clamp for the 60° average emergence angle of FU. This new adjusted graph is illustrated with the dashed line 615, where the value of the minimum approach angle has been appropriately adjusted for all values of the emergence angles in-between new input point 610 and the original input for 65° angle clamp.

Conversely, if the user wants to adjust a minimum approach angle for a particular follicular unit to be greater, for example, by 5° higher than the default, this situation is illustrated by the alternative dashed line 625 in FIG. 6. In this example, the user provided new input for adjustment of the minimum approach angle to be raised to 65° for the follicular unit having 50° emergence angle—see point 620. The processor is then able to automatically adjust other minimum approach angles and reconstruct the graph based on this new adjusted point 620 and by keeping the original default 40° angle clamp for the 20° average emergence angle of FU. This new adjusted graph is illustrated with the dashed line 625, where the value of the minimum approach angle has been appropriately adjusted for all values of the emergence angles in-between new input point 620 and the original input for 40° angle clamp.

As shown in the adjusted graphs 615 and 625 of FIG. 6, in both cases the user input is elegantly used in applying automated determination of the appropriate minimum approach angles and automatically or semi-automatically adjusting the angle parameter accordingly.

It will be appreciated that although the embodiment above has been described with respect to a minimum approach angle, a maximum approach angle (or maximum angle clamp) can also be determined and used in some embodiments. This maximum approach angle can be used, for example, to dictate the tool angle that should be utilized for follicular units that emerge at an angle above the maximum approach angle. For example, if the emergence angle of the follicular unit of interest is greater than a maximum approach angle, the tool may be oriented to the maximum approach angle. As a specific example, a maximum clamp angle of 65 to 70 degrees (e.g., 67°) may be imposed, such that for a follicular unit that emerges from the body surface at 75 degrees, the tool will be orientated at 67 degrees, and not to 75 degrees, even though 75 degrees is above the minimum clamp angle.

It should be noted that although many of the above examples and embodiments related to hair transplantation describe the tool being oriented relative to a follicular unit of interest, in other instances the tool may be oriented relative to an implantation site, or recipient area where a hair graft is to be implanted. It will be apparent that controlling and adjusting the orientation of a tool during an automated or semi-automated procedure and various examples and descriptions provided above are useful and applicable not only for hair harvesting or removal, but also for orienting the tool for making an implantation site, or for implanting hair. It is also applicable to applications other than hair transplantation, such as those already mentioned in the description, and including, for instance, procedures involving orientation of a needle for insertion into a body or an organ, such as an eye, or orienting a needle or other instrument relative to a vein or artery, and modifying the approach angle to compensate, for example, for motion or breathing.

According to another aspect of the present application, by analyzing the status of one parameter, it may be determined that some other parameter of the procedure should be modified. For example, as indicated in FIG. 3, the value W of the coring depth (CD) can be modified, modifying for example the depth to which the coring needle penetrates the body surface, the depth used to dissect the follicular unit from its surrounding tissue. A coring depth range of, for example, between 8 mm and 9 mm is common to achieve the desired dissection level of the subcutaneous fat. If the coring depth setting is set too high, a typical pattern of damage is a transection in the lower portion of the hair follicle. On the other hand, the coring depth may be set too low. In this situation this value may be modified, for example, if the second supplemental image 355 indicates that the "harvested" follicular unit is not being sufficiently elevated after the harvesting attempt. Therefore, by analyzing one parameter, such as the elevation of the follicular unit, it may be desirable to modify another parameter, such as the coring depth (CD) of the harvesting tool. The value X of the angle of the harvesting tool can be modified as well. This value may be modified, for example, if the second supplemental image 355 indicates that the attempts to harvest follicular units are transecting the follicular units. The value Y associated with the speed at which the harvesting tool rotates, RPM, may be modified, for example, if the second supplemental image indicates that the body surface is being torn. The value Z associated with the force at which the harvesting tool is forced into the body surface to penetrate the skin may also be modified in a similar manner. Rather than or in addition to modifying the value of Z, however, the user may utilize the information he has acquired to modify the tensioning of the skin surface rather than the force. That is, he or she may take the opportunity to alter the amount of tension applied by a skin tensioning device (if such device is used), or perhaps employ an alternative skin tensioning device. It will be apparent therefore that the modification need not necessarily directly relate to the identified parameter but indirectly do so, such that the modification enhances the results of the harvesting procedure. In some instances, modification of one parameter, may also affect the value of another parameter. Modification of the force applied to the punch is one such example since modifying the skin tension in response to discerning information from the supplemental images may cause better penetration, and hence have the potential to alter the actual resulting depth of penetration. Moreover, the value of the parameter being analyzed or the parameter to be modified does not need to be displayed.

In the event that the value Z of the force FC, at which the harvesting tool is forced to penetrate or advance through the layers of skin to dissect tissue, is modified to increase the force applied, yet no increase in coring depth CD results, using the parameters displayed, or otherwise determined or calculated, the user can make a decision (or the system may suggest a decision) to perhaps, rather than try increasing the value of the force FC again, to select another harvesting tool, perhaps one with a larger diameter punch, or a punch of different parameters.

The above-described example illustrates a harvesting tool comprising two harvesting needles (a sharper piercing punch and a coring/dissecting punch). The methods described herein, however, can equally apply to a single-needle harvesting tool. In this configuration of the harvesting tool the user display may provide a selection for a single punch, such as needle 200. Such selection is shown by example as 375 in FIG. 3. If a punch similar to the punch 200 with graduation markings 210 was utilized, using a snapshot like a first supplemental image 345 would allow a user (or the system itself as described above) to ascertain how deep into the body surface the punch 200 was penetrating. Should the user determine that the depth of penetration was too deep, the user may choose to reduce the penetration depth by, for example, using a mouse to click on an arrow (365) on the panel 370, which is associated with the penetration or puncture depth (PD) of the punch 200. Once the user clicks this arrow 365, the value V associated with the penetration depth (PD) is modified, and the program is able to execute that instruction, communicating that modification to the controller such that the penetration depth PD of the punch 200 is modified.

Various other features may be incorporated onto the user display, to facilitate the successful automated transplantation of hair while ensuring safety and control of the system to the user. For example, a STOP feature 380 may be incorporated, enabling the user to stop the hair transplantation procedure being carried out at any step within the procedure, though it will be appreciated that the system may be programmed to stop in certain instances, for example, at a point when the needle is retracted from the patient's body surface. Also, all parameters entered in the system may be cleared by clicking on the "clear" icon 385 before entering a new set of parameters. To begin the hair transplantation procedure one may select icon 390. It can be seen from FIG. 3, that the system may include many other control icons, none, some or all of which may be utilized in any one procedure.

In some embodiments, the memory of the system may only allow a predetermined number of image sets to be stored (at least temporarily or permanently) for later retrieval or use, or may allow all, or a subset of all harvest attempts to be stored. In another embodiment, using the mouse, the user may click an icon on the display to recall the last five, for example, image sets, thus visualizing the last five harvest attempts which may be displayed to the user, and parameters associated with the quality of the hair transplantation system or the procedure. In another aspect, the computer program may be configured to not only retrieve the images stored, but to list the values of the parameters associated with the hair harvesting process.

Figure 4:
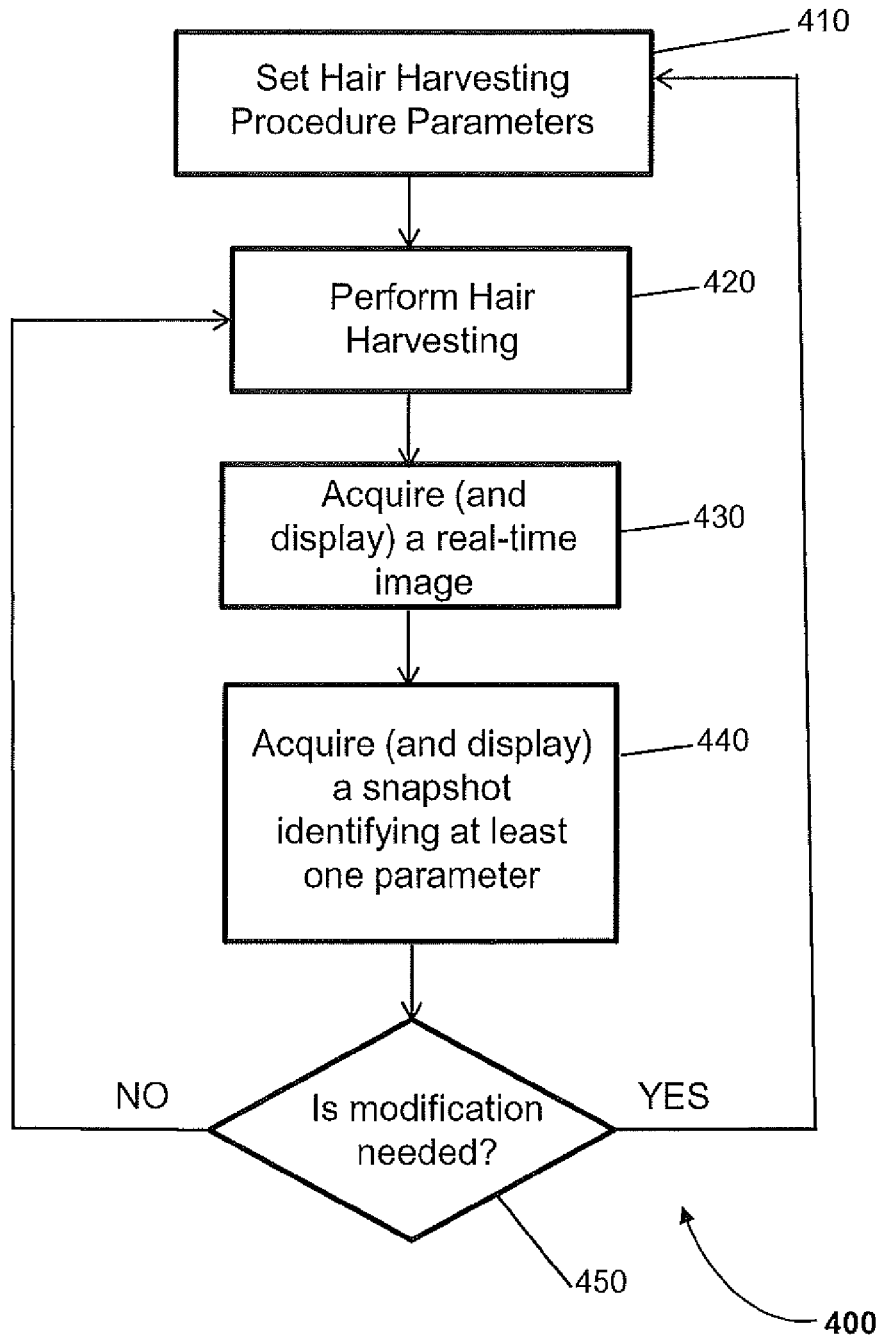
FIG. 4 is a block diagram illustrating an example of a general methodology according to one aspect of the invention.

FIG. 4 is a block diagram illustrating an example of a general methodology 400 employed by the present invention, as applied to hair harvesting example, though it will be apparent that the steps can equally be applied to the hair implantation procedure, or other appropriate procedure, with the necessary modifications. First, at step 410, before the hair harvesting procedure begins, parameters for the hair harvesting procedure may be selected, the parameters may include, but are not limited to, the force that is to be applied to the punch needle, the revolutions per minute associated with the punch needle, the depth of penetration of the punch needle, the revolutions per minute associated with the dissection needle, and the depth of penetration of the dissection needle. These parameters may be selected by the user, or the system may suggest a set of parameters from the memory, for example, based on the demographic patient data. Having selected these initial parameters, the automated hair harvesting procedure begins in step 420 by performing one or more hair harvesting attempts or events. As procedure is being performed, a real time image of the procedure may be acquired and may be displayed, as shown in step 430. It will be appreciated that in some embodiments due to a substantial automation it may not be required to show the real time image to the user, so the display aspect of this step may be optional, although it is anticipated that a real time image will be a useful feature to provide to the user, even if it is not required for the operational function of the automated system. As previously explained and described, in addition to the real-time image, in step 440 one or more supplemental images or historic snapshots may be acquired and displayed for some or all individual hair harvesting events. The timing of the supplemental snapshots is dictated by the parameter or the parameters of the hair harvesting procedure the value of which the snapshot is intended to ascertain, for example, the time of penetration of the skin by the harvesting punch. Again, in certain embodiments where modifications are made automatically by the system, displaying the snapshots to the user is not required for the operational function of the automated system, but it is still a useful feature for allowing the user to override the automatic selection. If it is determined in step 450 that no modification of any parameter of the hair harvesting procedure is needed, the harvesting procedure continues for one or more hair harvesting events. However, if it is determined in step 450 that at least one parameter associated with the hair harvesting procedure needs to be modified to improve the results of the procedure, whether the modification is by the user or an automated modification, the method returns to step 410, where the modification to the value of the hair harvesting parameter is made, prior to performing the next hair harvesting event in step 420. As indicated earlier, depending on a desired setting or upon the speed of this methodology, even though a value of a parameter may be modified in step 410, it may not necessarily affect the hair harvesting procedure performed on the next hair that is attempted to be harvested, but will affect a certain subsequent hair. It should be noted that by identifying in the snapshot the state of one parameter of the hair harvesting process, it may be determined that this and/or some other parameter should be modified, as described above in reference to FIG. 3.

According to one general aspect of the present application, a method for determining a need to modify a parameter of an automated procedure is provided. The method comprises providing and/or displaying a real-time image of a surface having an automated procedure performed thereon and also providing and/or displaying at least one historic snapshot of the surface, the snapshot identifying or allowing to ascertain/determine a parameter of the automated procedure. The method further comprises modifying the same or a different parameter of the automated procedure to improve the results of such procedure, for example, if a value of the parameter in the snapshot is outside one or more acceptable limits or otherwise less desirable. In some embodiments the value of the parameter may be modified or adjusted with a user input, in other embodiments, the modification may be performed automatically. For example, the processor may register the value of the parameter and compare it to a predetermined or selected acceptable value. If the difference is above a predetermined maximum threshold value, below a predetermined minimum threshold value, or falls outside a predetermined specified range of values, the processor may determine an adjustment to be necessary, and automatically apply the necessary modification to the parameter or another appropriate parameter. The method may comprise providing a modification interface that allows a user to modify one or more parameters of the automated procedure. Various examples of the parameters of interest have been described in reference to various procedures. For example, in reference to hair transplantation modification of parameter(s) may be directed to improving dissection of the follicular units. The parameters of interest may comprise a depth of insertion of the harvesting needle, or the angle of insertion, or centering of the needle relative to the follicular unit, or the force or rotational speed of the needle movement, or ability of the needle to dissect and at least partially elevate the follicular unit from the skin surface. In reference to removing color tattoos, such parameter of interest may be, for example, a laser wavelength and/or intensity. In some applications of the method, the automated procedure is an automated tattoo removal procedure and the modification interface allows the user to modify the intensity or wavelength of a light source. In other applications of the method, the automated procedure is an automated hair removal procedure and the modification interface allows the user to modify the intensity or wavelength of a light source.

According to another aspect, a method for determining a need to modify a parameter of an automated procedure, for example, hair transplantation procedure is provided. The method comprising providing a snapshot of a body surface, the snapshot displaying, for example, an indication of a maximum depth or angle of penetration or insertion of a tool (e.g., hair transplantation tool) with respect to the body surface. The method further comprises allowing for comparison of the displayed indication of depth or angle of insertion against an intended value of depth or angle of insertion and based on the comparison for determination of whether an adjustment of the depth or the angle of penetration is required. In some embodiments the determination is carried out automatically by a processor, the processor being part of an automated system. In other embodiments, determination is accomplished with a user input through a modification interface, or by combination of the user input and automatically by the system. The method may further comprise providing a second snapshot of the body surface, the second snapshot taken when a distal end of the tool is retracted from the body surface; and based on the second snapshot, determining if a procedure event, for example hair transplantation event, meets an intended hair transplantation criteria. In some embodiments the criteria may be a centering of the hair transplantation tool with respect to a follicular unit. Centering of the hair transplantation tool with respect to a follicular unit typically reduces the chances of damaging the dissected hair. To determine whether the intended hair transplantation criteria (e.g. centering) is met, one may compare an actual value indicative of the centering or a value associated with the centering of the hair transplantation tool with respect to the follicular unit, with an intended or desired value of the centering of the hair transplantation tool with respect to the follicular unit. In other embodiments the criteria may be no transection of the dissected follicular unit. In yet other embodiments the criteria may be an elevation of a follicular unit from the body surface, and determination comprises comparing a parameter indicative of the elevation of a follicular unit from the body surface with an intended value of the elevation of a follicular unit from the body surface. Once a determination has been made that the hair transplantation criteria has not been met (typically falling outside one or more acceptable or desirable limits), a parameter that influences the criteria can be modified such that the resulting dissection of the follicular unit is improved. For example, if it found that follicular units are not being sufficiently elevated from the body surface (that is, the elevation criteria is not being met), the puncture depth may be modified (for example, by increasing it), such that subsequent elevation depths meet the desired criteria, alternatively the force at which the harvesting punch penetrates the body surface can be increased or decreased as desired. It will be apparent to the reader that there are may be more than one parameter or combination of parameters that can be modified to influence hair transplantation criteria.

According to a further aspect of the present application, a method for determining the need to modify a parameter of an automated or partially automated procedure is provided. The method comprises processing information to enable the identification of, or to allow information to be determined with respect to, a parameter of the automated procedure. The method further comprises modifying the same or a different parameter of the automated procedure to improve the results of such procedure, for example, if a value of the parameter is outside one or more acceptable limits or otherwise less desirable. In some embodiments the value of the parameter may be modified or adjusted with a user input, in other embodiments, the modification may be performed automatically.

The present application is also directed to a method for automatically or semi-automatically modifying or determining the need to modify a depth of tool penetration of a body surface or tissue in at least partially automated procedure, for example, a hair transplantation procedure. The method comprises providing or processing information to enable modification of the tool penetration depth, if certain conditions are met. In some embodiments, the tool has graduation marks, and the method further comprises modifying the tool penetration or puncture depth if the number of, or portion of, the graduation marks above the surface being penetrated is outside one or more acceptable or desirable limits. In other embodiments, the method further comprises modifying the depth of penetration of the tool based on the historic stored information of the prior tool depth adjustments, including average adjustments in the area in close proximity to the current proposed location of the procedure.

The present application is also directed to a method for automatically or semi-automatically modifying or determining the need to modify an approach angle of a tool in at least partially automated procedure, for example, a hair transplantation procedure. The method comprises providing or processing information to enable modification of the tool approach angle, if certain conditions are met. In some embodiments, the method comprises selecting an angle clamp or minimum approach angle of the tool. The method may further comprise implementing an interpolation procedure to provide the suggested values for the angle clamps, wherein the interpolation procedure comprises interpolating between at least two angle clamps. In a further embodiment, the at least two angle clamps (or minimum approach angles) may be input by the user via a user interface. With reference to hair transplantation, the method may comprise selecting an angle clamp for each of at least two emergence angles of the follicular units, and determining, for example, by interpolation, a plurality of additional angle clamps for each of the plurality of the emergence angles of the follicular units with the value between the values of the at least two emergence angles.

It will be apparent that the number of steps that are utilized for such methods are not limited to those described above. Also, the methods do not require that all the described steps are present. Although the methodology described above as discrete steps, one or more steps may be added, combined or even deleted, without departing from the intended functionality of the embodiments of the invention. The steps can be performed in a different order or have the steps shared between more than one processor, for example. It will also be apparent that the method described above may be performed in a partially or substantially automated fashion, including performed using robotic systems.

As will be appreciated by those skilled in the art, the methods of the present invention may be embodied, at least in part, in software and carried out in a computer system or other data processing system. Therefore, in some exemplary embodiments hardware may be used in combination with software instructions to implement the present invention.

The processor for use in the present invention may comprise any suitable device programmed and configured to perform various methods described in detail in the present application, including methods directed to modifying a parameter of a hair harvesting or implanting procedure to improve results of the procedure, for example, if the same or other identified parameter associated with the procedure is unacceptable. In some embodiments modification may be accomplished through the modification interface. For example, the processor for use in the present invention may be a processor comprising a set of instructions for executing operations, the set of instructions including instructions for processing one or more images of a body surface to identify and/or display a parameter (or a plurality of parameters) associated with, for example, the hair transplantation procedure, and for modifying or allowing to modify such parameter (or other parameters) as may be necessary or desirable to successfully carry out the procedure. The system for use according to the inventions described herein may comprise in addition to a processor an image acquisition device. For example, a system for determining a need to modify a parameter of an automated hair transplantation procedure may be provided. The system may comprise a user interface including a processor, the processor configured to process a snapshot of a body surface which provides an indication of a depth or angle of penetration of a hair transplantation tool with respect to the body surface, and to allow for comparison of the indicated depth or angle of penetration against an intended value of the depth or the angle of penetration.

In some embodiments, the system may comprise a user input device, the user input device configured to allow a user to interactively modify the depth or angle of penetration of the hair transplantation tool based on the comparison. In other embodiments, the processor is configured to automatically modify the depth or angle of penetration of a hair transplantation tool based on the comparison, for example, to bring the future depth of penetration or the angle of the tool within a predetermined deviation from the intended value.

Certain embodiments relate to a machine-readable medium (e.g., computer readable media) or computer program products that include program instructions and/or data (including data structures) for performing various computer-implemented operations. A machine-readable medium may be used to store software and data which causes the system to perform methods of the present invention. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. I may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

The various embodiments described above are provided by way of illustration only and should not be construed to limit the claimed invention. Those skilled in the art will readily recognize various modifications and changes that may be made to the disclosed embodiments without departing from the scope of the claimed invention. By way of non-limiting example, it will be appreciated by those skilled in the art that particular features or characteristics described in reference to one figure or embodiment may be combined as suitable with features or characteristics described in another figure or embodiment. Further, those skilled in the art will recognize that the devices, systems, and methods disclosed herein are not limited to the fields described by example in the present application. The description, therefore, is not to be taken in a limiting sense.

It will be further appreciated by those skilled in the art that the invention is not limited to the use of a particular system, and that various automated (including robotic), or partially or semi-automated systems and apparatus may be used for positioning and actuating the respective removal tools and other devices and components disclosed herein.

The foregoing illustrated and described embodiments of the invention are susceptible to various modifications and alternative forms, and it should be understood that the invention generally, as well as the specific embodiments described herein, are not limited to the particular forms or embodiments disclosed, but to the contrary cover all modifications, equivalents and alternatives falling within the scope of the appended claims. Applicant regards the subject matter of the invention to include all novel and nonobvious combinations and subcombinations of the various elements, features, functions, and/or properties disclosed herein.

What is claimed is:

1. A method for modifying a parameter of operation of an apparatus for use in an at least partially automated procedure comprising a plurality of repetitive events, the method comprising:

generating a real-time image of a patient body surface where an image-guided apparatus comprising a tool is used to perform an at least partially automated procedure, the at least partially automated procedure comprising a plurality of repetitive events occurring too fast for a user to discern whether a criterion associated with the at least partially automated procedure is met;

generating at least two historic snapshots of the patient body surface based on the real-time image, the at least two historic snapshots allowing to identify whether the criterion associated with the at least partially automated procedure on the patient body surface is met, wherein the timing of the at least two historic snapshots is automatically controlled by a processor such that a first of the at least two historic snapshots comprises an image acquired at a first moment in time after the tool of the image-guided apparatus has penetrated the patient body surface during occurrence of an event of the plurality of repetitive events, and a second of the at least two historic snapshots comprises an image acquired at a second moment in time associated with substantial completion of the event; and without interrupting the at least partially automated procedure, modifying at least one parameter of operation of the apparatus for a subsequent event of the plurality of the events if the criterion associated with the at least partially automated procedure is not met for the event, as identified from the at least two historic snapshots of the event.

2. The method of claim 1, wherein modification of the at least one parameter influences the criterion.

3. The method of claim 1, comprising determining and displaying a value associated with the criterion.

4. The method of claim 1, wherein the criterion comprises centering of a tool with respect to an object of the at least partially automated procedure.

5. The method of claim 1, wherein the criterion comprises whether an object of the at least partially automated procedure was damaged during the procedure or elevation of a tool used during the at least partially automated procedure from the body surface.

6. The method of claim 1, wherein identifying the criterion comprises visual or calculated identification.

7. The method of claim 1, wherein the first historic snapshot is captured when the tool has penetrated the patient body surface to a maximum depth of penetration, or at a predetermined time interval after activation of the tool.

8. The method of claim 1, wherein the tool is fully or semi-automated, and the method further comprises controlling movement of the tool at least in part using a mechanical system, electromechanical system, a pneumatic system, hydraulic system, or a magnetic system.

9. The method of claim 1, wherein modifying is accomplished automatically, the method further comprising registering a value of the criterion and comparing the registered value to a predetermined value, and if the difference between the registered value and the predetermined value is outside an acceptable range, determining the at least one parameter to modify.

10. The method of claim 1, wherein modifying is accomplished with a user input through a modification interface, the modification interface comprising a keyboard a mouse, a voice or speech recognition device, a laser pointer, touch screen, tablet computer, personal digital assistant (PDA), or a remote user input device.

11. The method of claim 9, the method comprises prompting the user to accept automatically determined parameter modification and automatically making such modification if the user accepts the determined parameter modification.

12. The method of claim 1, wherein a value of the criterion comprises a depth that a tool having graduation markings penetrates the body surface, the method further comprising modifying the depth if the number of, or portion of, the graduation markings above the body surface is outside one or more acceptable or desirable limits.

13. The method of claim 1, wherein the at least partially automated procedure is a hair transplantation procedure, a site making procedure, a tattoo placement or removal procedure, an ablation procedure, a cosmetic injection procedure, an ophthalmic procedure, or procedure for treating dermatological condition.

14. The method of claim 1, wherein the apparatus comprises a robotic system having the tool operatively coupled to a robotic arm, and the method further comprises controlling movement of the tool under control of program instructions executed by a processor.

15. The method of claim 1, further comprising clearing one or more of the parameters of operation of the apparatus before entering a new set of parameters.

16. The method of claim 1, comprising acquiring data at an instant in time.

17. The method of claim 1, further comprising providing at least another snapshot of the body surface allowing to identify a value of the modified parameter.

18. The method of claim 1, wherein if a location of a current procedure site is outside a predetermined distance from one or more previous procedure sites, the method further comprises determining whether to modify the at least one parameter of operation of the apparatus for the current procedure if a value of the criterion is outside one or more acceptable or desirable limits.

19. The method of claim 1, wherein the at least one parameter comprises a tool approach angle of the tool used in performing the at least partially automated procedure.

20. The method of claim 19, wherein the at least partially automated procedure is a hair transplantation procedure and the method further comprises determining if the tool approach angle needs to be modified based at least in part on a result of comparison of a minimum or maximum approach angle of the tool and an emergence angle of a hair graft.

21. The method of claim 20, wherein the minimum or maximum approach angle is automatically selected based on an average emergence angle of a plurality of hair grafts in an area on a body surface or is based on an interpolation procedure between correspondingly at least two minimum or at least two maximum approach angles.

22. The method of claim 20, wherein if the emergence angle of the hair graft is less than the minimum approach angle and a difference between the minimum approach angle and the emergence angle of the hair graft is less than a predetermined value, the tool is oriented at an angle which is substantially equal to the sum of the predetermined value and the emergence angle of the hair graft.

23. A method for determining a need to modify a parameter of an at least partially automated hair transplantation procedure, the method comprising:
processing a real-time image of a surface having an at least partially automated hair transplantation procedure performed thereon;
processing at least one snapshot of the surface, the at least one snapshot identifying a tool approach angle of a tool used in performing the at least partially automated hair transplantation procedure; and
determining if a value of the tool approach angle or a different parameter associated with the at least partially automated hair transplantation procedure is outside one or more acceptable or desirable limits and whether the tool approach angle needs to be modified based at least in part on a result of comparison of a minimum or maximum approach angle of the tool and an emergence angle of a hair graft,
wherein if the emergence angle of the hair graft is less than the minimum approach angle and a difference between the minimum approach angle and the emergence angle of the hair graft is less than a predetermined value, the tool is oriented at an angle which is substantially equal to the sum of the predetermined value and the emergence angle of the hair graft.

24. The method of claim 23, comprising determining and/or displaying a value associated with the tool approach angle or the different parameter.

25. The method of claim 23, wherein if the emergence angle of the hair graft is the same or more than the minimum approach angle, the method comprising orienting the tool at an angle which is substantially equal to the emergence angle of the hair graft.

26. The method of claim 23, wherein if the emergence angle of the hair graft is more than the minimum approach angle and a difference between the minimum approach angle and the emergence angle of the hair graft is more than the predetermined value, the method comprising orienting the tool at an angle which is not more than the sum of the predetermined value and the minimum approach angle.

27. The method of claim 23, wherein if the emergence angle of the hair graft is more than the maximum approach angle, the method comprising orienting the tool at an angle substantially equal to the maximum approach angle.

28. The method of claim 23, comprising choosing the minimum or maximum approach angle of the tool based at least in part on an average or mean emergence angle of a plurality of hair grafts in an area.

29. The method of claim 23, comprising automatically selecting the minimum or maximum approach angle based on an interpolation procedure between correspondingly at least two minimum or at least two maximum approach angles.

30. The method of claim 23, wherein the minimum or maximum approach angle is user-specified or based on historic data.

31. The method of claim 23, wherein the minimum or maximum approach angle is automatically determined, the method further comprising allowing the user to interactively adjust the automatically determined minimum or maximum approach angle.

32. An image-guided apparatus for performing at least partially automating a procedure, the image-guided apparatus comprising:
a tool configured to penetrate a body surface and perform a plurality of repetitive events;
a computing system configured to control, at least partially, movement of the tool during each of the plurality of repetitive events according to one or more parameters of operation, the plurality of repetitive events occurring at a rate that is too fast for an operator of the image-guided apparatus to accurately discern whether the one or more parameters of operation of the tool should be modified if a criterion associated with the at least partially automated procedure is not met; and
an image acquisition device configured to generate images of the body surface;
wherein the computing system is programmed to use the image acquisition device to acquire a snapshot of a body surface at a point in time after the tool has penetrated the body surface during an event of the plurality of repetitive events to enable determining, without interrupting the at least partially automated procedure, whether the one or more parameters of operation of the tool should be modified.

33. The image-guided apparatus of claim 32, wherein the computing system is programmed to generate a suggested modification of the one or more parameters of operation of the tool based at least partly on an automated analysis of the snapshot.

34. The image-guided apparatus of claim 33, wherein the computing system is programmed to output the suggested parameter modification to the operator and wherein the image-guided apparatus comprises a user interface configured to enable the operator to accept or reject the parameter modification suggested by the computing system.

35. The image-guided apparatus of claim 32, wherein the computing system is programmed to display the snapshot on a display screen together with a user interface configured to enable the operator to modify the one or more parameters of operation of the tool based on the snapshot.

36. The image-guided apparatus of claim 35, wherein the computing system is programmed to acquire two snapshots at two respective points in time during the occurrence of an event of the plurality of repetitive events, and to concurrently display both snapshots on the display screen to enable the operator to discern whether the criterion associated with the at least partially automated procedure is met.

37. The image-guided apparatus of claim 36, wherein the second snapshot is acquired at a second moment in time associated with substantial completion of the event.

38. The image-guided apparatus of claim 32, wherein the criterion relates to at least one of the following: a) whether an object of the at least partially automated procedure was damaged during the event, b) a force applied to the tool, c) elevation of an object of the at least partially automated procedure from the body surface, or d) centering the tool with respect to an object of the at least partially automated procedure.

39. The image-guided apparatus of claim 32, wherein the computing system is programmed to acquire the snapshot at a point in time at which the tool has penetrated the body surface to a maximum depth of penetration during the event of the plurality of repetitive events.

40. The image-guided apparatus of claim 32, wherein the computing system is programmed to acquire the snapshot at a point in time at which the tool is withdrawn from the body surface during the event.

41. The image-guided apparatus of claim 32, wherein the image-guided apparatus comprises a robotic system comprising a robotic arm and the tool is coupled to the robotic arm.

42. The image-guided apparatus of claim 32, wherein the at least partially automated procedure is hair transplantation procedure and the event of the plurality of repetitive events is a hair harvesting event, a site making event, or a hair implantation event.

43. The image-guided apparatus of claim 32, wherein the at least partially automated procedure is a tattoo placement or removal procedure, an ablation procedure, a cosmetic injection procedure, or procedure for treating dermatological condition.

* * * * *